United States Patent [19]
Hechinger

[11] Patent Number: 6,159,748
[45] Date of Patent: Dec. 12, 2000

[54] EVALUATION OF AUTOIMMUNE DISEASES USING A MULTIPLE PARAMETER LATEX BEAD SUSPENSION AND FLOW CYTOMETRY

[75] Inventor: Mark K. Hechinger, Pasadena, Calif.

[73] Assignee: AffiniTech, LTD, Bentonville, Ark.

[21] Appl. No.: 09/088,648

[22] Filed: Jun. 1, 1998

Related U.S. Application Data

[63] Continuation-in-part of application No. 08/404,144, Mar. 13, 1995, abandoned.

[51] Int. Cl.[7] ............................. G01N 33/543; C12Q 1/70
[52] U.S. Cl. ......................... 436/518; 436/501; 436/506; 436/507; 436/509; 436/513; 436/528; 436/531; 436/533; 436/534; 436/546; 436/523; 436/805; 436/811; 435/5; 435/6; 435/7.1; 435/7.94; 435/810
[58] Field of Search ........................... 435/5, 6, 7.1, 7.94, 435/810; 436/501, 506, 507, 509, 513, 518, 528, 531, 533, 534, 546, 523, 805, 811

[56] References Cited

U.S. PATENT DOCUMENTS

| | | | |
|---|---|---|---|
| 3,088,875 | 5/1963 | Fisk | 167/84.5 |
| 3,551,555 | 12/1970 | Schuurs | 424/12 |
| 3,658,982 | 4/1972 | Reiss et al. | 424/12 |

(List continued on next page.)

FOREIGN PATENT DOCUMENTS 1561042  2/1980  United Kingdom ........................ 33/48

OTHER PUBLICATIONS

Bonfa, Golombek, Kaufman, Skelly, Weissbach, Brot, and Elkon; Association Between Lupus Phychosis and Anti–Ribosomal P Protein Antibodies; New England Journal of Medicine, Jul. 30, 1987; vol. 317 No. 5; pp. 265–271.

Elkon and Jankowski; Fine Specificities of Autoantibodies Directed Against the Ro, La, Sm, RNP, and Jo–1 Proteins Defined by Two–Dimensional Gel Electrophoresis and Immunoblotting; The Journal of Immunology; Jun., 1985; vol. 134, No. 6; pp. 3819–3824.

Fulwyler and McHugh; Flow Microsphere Immunoassay for the Quantitative and Simultaneous Detection of Multiple Soluble Analytes; Methods in Cell Biology, vol. 33; Chapter 51; 1990; Academic Press, Inc.; pp. 613–629.

(List continued on next page.)

Primary Examiner—Christopher L. Chin
Assistant Examiner—Pensee T. Do
Attorney, Agent, or Firm—Head, Johnson & Kachigian

[57] ABSTRACT

Immunoassay methods and apparatus are provided which utilize flow cytometry, coated latex microspheres, and labelled antibodies, to simultaneously detect the presence and amount of several antigens or antibodies in a sample. Microspheres can be sized by forward angle light scatter (FALS) or electronic volume. By combining FALS and fluorescence, it is practical to use beads of several different sizes, colors or shapes, each bead coated with a different protein or antibody, for the simultaneous detection of multiple analytes in a sample. Available auto-sampling systems make it even more appealing in this regard. In accordance with one embodiment, highly purified RNP. Sm, SS-A, SS-B and Scl-70 antigens are bound to 4, 5, 6, 7 and 10 $\mu$m latex beads, respectively and stabilized for extended shelflife. Diluted patient serum is placed into test tubes containing a mixture of the five antigen coated beads and incubated. If an antibody is present for a specific antigen, it will bind to that specific bead. After washing the bead/serum mixture to remove residual sample, a second incubation with goat anti-human IgG, conjugated with a fluorochrome, is carried out. This conjugate will bind immunologically to the anti-antigen IgG of the antigen-antibody complex. forming a "sandwich" consisting of bead—antigen—primary antibody—secondary antibody—FITC. The fluorescence intensity is based on the avidity of the bead/antibody/conjugate binding. The samples are analyzed using a flow cytometer.

12 Claims, 22 Drawing Sheets

BEAD DETECTION SYSTEM

U.S. PATENT DOCUMENTS

| | | |
|---|---|---|
| 3,666,421 | 5/1972 | Price .......................................... 23/253 |
| 3,826,613 | 7/1974 | Parikh et al. .............................. 23/230 |
| 3,992,517 | 11/1976 | Lowke et al. .............................. 424/12 |
| 4,055,633 | 10/1977 | Goldstein ................................... 424/1 |
| 4,181,636 | 1/1980 | Fischer ....................................... 260/8 |
| 4,234,563 | 11/1980 | Rippe .......................................... 424/8 |
| 4,254,097 | 3/1981 | Rippe .......................................... 424/8 |
| 4,279,617 | 7/1981 | Masson et al. ............................ 23/230 |
| 4,351,824 | 9/1982 | Lehrer ........................................ 424/12 |
| 4,659,659 | 4/1987 | Dwek et al. ................................ 435/18 |
| 4,665,020 | 5/1987 | Saunders .................................... 435/7 |
| 4,751,181 | 6/1988 | Keene ........................................ 435/70 |
| 4,751,188 | 6/1988 | Valet .......................................... 436/63 |
| 4,784,942 | 11/1988 | Harley ........................................ 435/7 |
| 4,812,397 | 3/1989 | Weisbart .................................... 435/7 |
| 4,965,250 | 10/1990 | Vincent et al. ............................ 514/18 |
| 4,988,676 | 1/1991 | Platsoucas ................................ 514/21 |
| 5,049,659 | 9/1991 | Cantor et al. ............................ 530/351 |
| 5,162,863 | 11/1992 | Ito ............................................. 356/73 |
| 5,238,839 | 8/1993 | Cantor et al. ......................... 435/240.1 |
| 5,239,062 | 8/1993 | Blattler et al. .......................... 530/369 |
| 5,286,452 | 2/1994 | Hansen ...................................... 422/73 |
| 5,380,663 | 1/1995 | Schwartz et al. ......................... 436/10 |
| 5,405,784 | 4/1995 | Van Hoegaerden ..................... 436/523 |
| 5,518,882 | 5/1996 | Lund et al. ................................. 436/6 |
| 5,525,525 | 6/1996 | Hokama ................................. 436/523 |

OTHER PUBLICATIONS

Halbwachs–mecarelli, Nusbaum, Noël, Reumaux, Erlinger, Grünfeld and Lesavre; Antineutrophil Cytoplasmic Antibodies (Anca) Directed Against Cathepsin G in Ulcerative Colitis, Crohn's Disease and Primary Sclerosing Cholangitis; Clin. Exp. Immunol., (1992) vol. 90; pp. 79–84.

Horan, Schenk, Abraham, Kloszewski; Fluid Phase Particle Fluorescence Analysis: Rheumatoid Factor Specificity Evaluated by Laser Flow Cytophotometry; Immunoassays in the Clinical Laboratory; 1979, Alan R. Liss, Inc., 150 Fifth Avenue, New York, NY 1001; pp. 185–198.

Lim, Gumbert and Garovoy; A Flow Cytometric Method for the Detection of the Development of Antibody to Orthoclone Okt3; Journal of Immunological Methods; vol. 121; 1989; pp.197–201.

Lindmo, Bormer, Ugelstad and Nustad; Immunometric Assay By Flow Cytometry Using Mixtures of Two Particle Types Of Different Affinity; Journal of Immunological Methods, 126 (1990), pp. 183–189.

Lisi, Huang, Hoffman, and Teipel; A Fluorescence Immunoassay for Soluble Antigens Employing Flow Cytometric Detection; Clinica Chimica Acta; vol. 120 (1982) pp. 171–179.

McHugh and Stites; Application of Bead–based Assays for Flow Cytometry Analysis; Clinical Immunology Newsletter; vol. 11, No. 4; 1991, pp. 60–64.

McHugh, Stites, Busch, Krowka, Stricker, Hollander; Relation of Circulating Levels of Human Immunodeficiency Virus (HIV) Antigen, Antibody to P24 and HIV–containing Immune Complexes in HIV–infected Patients; the Journal of Infectious Diseases, vol. 158, No. 5, Nov., 1988; pp. 1088–1091.

McHugh, Stites, Casavant and Fulwyler; Flow Cytometric Detection and Quantitation of Immune Complexes Using Human Clq–Coated Microspheres; Journal of Immunological Methods, vol. 95 (1986); pp. 57–61.

McHugh, Miner, Logan and Stites; Simultaneous Detection of Antibodies to Cytomegalovirus and Herpes Simplex Virus by Using Flow Cytometry and a Microsphere–based Fluorescence Immunoassay; Journal of Clinical Microbiology; vol. 26, No. 10; Oct. 1988; pp. 1957–1961.

McHugh, Wang, Chong, Blackwood and Stites; Development of a Microsphere–based Fluorescent Immunoassay and its Comparison to an Enzyme Immunoassay for the Detection of Antibodies to Three Antigen Preparations from *Candida Albicans*; Journal of Immunological Methods; vol. 116 (1989); pp. 213–219.

Saunders, Jett and Martin; Amplified Flow–cytometric Separation–free Fluorescence Immunoassays; Clinical Chemistry; vol. 31, No. 12; (1985), pp. 2020–2023.

Saunders, Martin, Jett and Perkins; Flow Cytometric Competitive Binding Assay for Determination of Actinomycin–d Concentrations[1,2]; Cytometry; vol. 11; (1990); pp. 311–315.

Scillian, McHugh, Busch, Tam, Fulwyler, Chien and Vyas; Early Detection of Antibodies Against Rdna–produced Hiv Proteins with a Flow Cytometric Assay; Blood; vol. 73, No. 7; (May 15, 1989); pp. 2041–2048.

Shero, Bordwell, Rothfield, Earnshaw; High Titers of Autoantibodies to Topoisomerase I (Scl–70) in Sera from Scleroderma Patients; Science; vol. 231; (Feb. 14, 1986); pp. 737–740.

Van De Water, Cooper, Surh, Coppel, Danner, Ansari, Dickson, and Gershwin; Detection of Autoantibodies to Recombinant Mitochondrial Proteins in Patients with Primary Biliary Cirrhosis; the New England Journal of Medicine; vol. 320, No. 21; (May 25, 1989); pp. 1377–1380.

Wilson, Mulligan and Raison; A New Microsphere–based Immunofluorescence Assay for Antibodies to Membrane–associated Antigens; Journal of Immunological Methods; vol. 107 (1988) pp. 231–237.

Brochure; Immunovision the Source; Immunovision, Inc.; (1991–1992); 1506 Ford Avenue, Springdale, Arkansis AR 72764.

Nakamura, Peebles, Rubin, Molden, Tan; Autoantibodies to Nuclear Antigens (ANA) Advances in Laboratory Tests and Significance in Systemic Rhematic Diseases; (Second Edition); American Society of Clinical Pathologists; (1985); pp. 3, 4, 7, 12–15, 97.

McHugh, Thomas H.; Flow Microsphere Immunoassay for the Quantitative and Simultaneous Detection of Multiple Soluble Analytes; Methods in Cell Biology, vol. 42; Chapter 33; Dec. 1994; Academic Press, Inc.; pp. 575–595.

Horan and Wheeless, Jr.; Quantitative Single Cell Analysis and Sorting; Science, vol. 198; Oct. 14, 1977; Pp 149–157.

Poster Presentation, CMC, Meeting, Charleston, SC, 1995 Mark K. Hechinger.

Abstract: Immunobead/flow Cytometry Detection of Antinuclear Antibodies, 1996, Hechinger, M. K. et al.

"Dipstick" Test for *E. Coli*, Science, vol. 278, Dec. 12, 1997, p. 1887.

McDade and Fulton, True Multiplexed Analysis by Computer–Enhanced Flow Cytometry, Medical Device & Diagnostic Industry, Apr. 1997.

McHugh and Rectenwald, Detection of Antibody to HCV By Using a Microsphere Immunoassay; University of California, Dept. of Laboratory Medicine, Aug. 1996.

FIGURE 1 - BEAD DETECTION SYSTEM

Fig. 5 Microspheres of different sizes (4,5,6,7, and 10 μm) as seen with flow cytometer forward and side (90°) light scatter.

Fig. 6  Antigen labeled microspheres incubated with negative serum.

Fig. 7  Antigen labeled microspheres incubated with a serum containing antibody to Scl-70 but negative for antibodies to the four other antigens.

Fig. 8  Multi-color Bead Analysis using size and fluorescense

Fig 9  Schematic presentation illustrating combination of different bead sizes with two different fluorochromes for two color flow cytometry. Differences in bead sizes not shown, but would be seen in three dimensional plot.

Fig. 10 - Clinical Bead Trials - Sensitivity Graph with Mean Channel Fluorescence in EU/mL Positive Serum Dilutions

| Antigens | | 1:1 | 1:2 | 1:4 | 1:8 | 1:16 | 1:32 | 1:64 | 1:128 |
|---|---|---|---|---|---|---|---|---|---|
| | RNP | 82.6 | 100.2 | 118.9 | 136.3 | 131.5 | 164.8 | 208.3 | 186.9 |
| | | 95.0 | 47.5 | 23.8 | 11.9 | 5.9 | 2.9 | 1.5 | 0.8 |
| | SM | 86.0 | 100.6 | 125.5 | 137.6 | 158.4 | 197.5 | 197.3 | 177.9 |
| | | 100.0 | 50.0 | 25.0 | 12.5 | 6.3 | 3.2 | 1.6 | 0.8 |
| | SSA | 77.4 | 79.8 | 89.0 | 96.2 | 112.4 | 124.1 | 155.6 | 195.3 |
| | | 80.0 | 40.0 | 20.0 | 10.0 | 5.0 | 2.5 | 1.3 | 0.7 |
| | SSB | 54.8 | 64.4 | 70.4 | 76.7 | 86.5 | 105.3 | 120.5 | 155.0 |
| | | 80.0 | 40.0 | 20.0 | 10.0 | 5.0 | 2.5 | 1.3 | 0.7 |
| | SCL-70 | 72.6 | 90.5 | 97.8 | 107.4 | 111.0 | 127.8 | 164.9 | 151.9 |
| | | 110.0 | 55.0 | 27.5 | 13.8 | 6.9 | 3.5 | 1.8 | 0.9 |

RHEUMO-BEADS – RNP COMPARISON

RHEUMO-BEADS – SS-B COMPARISON

RHEUMO-BEADS – Scl–70 COMPARISON

```
Sample   : CONTROL MIX  001
Cytometer: FACSCAN
FL1      : CT                FL2:                    FL3 :
```

```
Sample   : CONTROL MIX  001
Cytometer: FACSCAN
FL1      : CT                FL2:                    FL3 :
```

Contour statistics

Sample     : CONTROL MIX  001
Parameters : FL1  FSC       Gated events :  9979        Total events :  10000

| # | X & Y Lower | X & Y Upper | Events | % Gated | % Tot | X & Y Mean | X & Y Mode | Peak |
|---|---|---|---|---|---|---|---|---|
| 1 | 1.00 21 | 18.61 63 | 3396 | 34.03 | 33.96 | 3.75 33.55 | 2.08 26.00 | 160 |
| 2 | 21.54 21 | 10000 63 | 42 | 0.42 | 0.42 | 29.61 46.86 | 21.54 33.00 | 4 |
| 3 | 1.00 0 | 18.61 20 | 6540 | 65.54 | 65.40 | 1.42 15.23 | 1.00 17.00 | 2143 |
| 4 | 21.54 0 | 10000 20 | 1 | 0.01 | 0.01 | 80.31 13.00 | 80.31 13.00 | 1 |
| 5 | 69.39 0 | 10000 63 | 4 | 0.04 | 0.04 | 84.40 43.25 | 69.39 63.00 | 1 |
| 6 | 21.54 0 | 10000 63 | 43 | 0.43 | 0.43 | 30.79 46.07 | 21.54 33.00 | 4 |

Sample   : MIX BEADS   002
Cytometer: FACSCAN
FL1      : NORMAL CT          FL2:                FL3 :

Sample   : MIX BEADS   002
Cytometer: FACSCAN
FL1      : NORMAL CT          FL2:                FL3 :

Contour statistics

Sample    : MIX BEADS   002
Parameters: FL1  FSC          Gated events :  9844        Total events :  10000

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9844 | 100.00 | 98.44 | 4.76 21.33 | 1.00 17.00 | 1827 |
| 2 | 69.39 0 | 10000 63 | 32 | 0.33 | 0.32 | 209.96 49.72 | 69.39 63.00 | 3 |

```
Sample   : MIX BEADS   003
Cytometer: FACSCAN
FL1      : RNP          FL2:                    FL3 :
```

```
Sample   : MIX BEADS   003
Cytometer: FACSCAN
FL1      : RNP          FL2:                    FL3 :
```

Contour statistics

| | Sample : MIX BEADS 003 | | | | | | |
|---|---|---|---|---|---|---|---|
| | Parameters : FL1 FSC | | Gated events : 9979 | | Total events : | 10000 | |
| # | X & Y Lower | X & Y Upper | Events | % Gated | % Tot | X & Y Mean | X & Y Mode | Peak |
| 1 | 1.00 0 | 10000 63 | 9979 | 100.00 | 99.79 | 29.07 21.65 | 28.86 13.00 | 408 |
| 2 | 69.39 0 | 10000 63 | 751 | 7.53 | 7.51 | 109.98 38.85 | 69.39 25.00 | 34 |

```
Sample   : MIX BEADS   006
Cytometer: FACSCAN
FL1      : SSB              FL2:              FL3 :
```

```
Sample   : MIX BEADS   006
Cytometer: FACSCAN
FL1      : SSB              FL2:              FL3 :
                    Contour statistics
Sample     : MIX BEADS   006
Parameters : FL1 FSC      Gated events : 9981      Total events : 10000
```

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9981 | 100.00 | 99.81 | 14.14 21.26 | 1.00 17.00 | 1856 |
| 2 | 69.39 0 | 10000 63 | 140 | 1.40 | 1.40 | 123.05 46.94 | 92.95 57.00 | 5 |

```
Sample   : MIX BEADS   007
Cytometer: FACSCAN
FL1      : SC7-70            FL2:              FL3 :
                        Contour statistics
Sample   : MIX BEADS   007
Parameters : FL1 FSC    Gated events : 9983    Total events : 10000
```

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9983 | 100.00 | 99.83 | 10.62 21.17 | 1.00 16.00 | 1686 |
| 2 | 69.39 0 | 10000 63 | 95 | 0.95 | 0.95 | 135.16 45.75 | 69.39 34.00 | 5 |

EVALUATION OF AUTOIMMUNE DISEASES USING A MULTIPLE PARAMETER LATEX BEAD SUSPENSION AND FLOW CYTOMETRY

CROSS-REFERENCE TO RELATED APPLICATIONS

This application is a continuation-in-part of U.S. patent application Ser. No. 08/404,144, filed Mar. 13, 1995, now abandoned.

BACKGROUND OF THE INVENTION

The present invention is directed to immunoassay methods and apparatus, and more particularly concerns an immunobead-flow cytometry method, apparatus, assay, device, system, kit, and the like for detecting and quantifying antigens or antibodies and especially adapted for the detection of autoantibodies to nuclear antigens associated with autoimmune diseases.

Typically, autoimmune testing for Systemic Lupus Erythematosis (SLE), Systemic Rheumatic Disease, rheumatoid arthritis, Sjogren's Syndrome, Progressive Systemic Sclerosis (PSS), Subacute Erythematosis, congenital complete heart block, neonatal complete heart block, neonatal lupus dermatitis, Polymyositis, Human Immunodeficiency Virus (HIV), Acquired Immunodeficiency Syndrome (AIDS), as well as other diseases has involved the use of extractable nuclear antigens (ENA) and immunological assays including hemagglutination, counter immunoelectrophoresis (CIE), immunodiffusion, Enzyme Linked Immunosorbent Assay (ELISA), and the like. For example, the Ro(SS-A) antigen having one major band at 60 kD by SDS gel electrophoresis (silver stain) has been purified through the use of immobilized human anti-Ro(SS-A) immunoglobulins. La(SS-B) antigen has two major bands, one at 40 kD and the other at 23 kD (a degradation product) by SDS gel electrophoresis (silver stain) and has been purified through the use of immobilized human anti-La(SS-B) immunoglobulin. Smith (Sm) antigen has two major bands in the 10 and 14 kD region by SDS gel electrophoresis (silver stain) has been purified through the use of immobilized human anti-Sm (Smith) immunoglobulins. Smith (Sm/RNP) antigen has five bands, one each at 70, 40, 24, 12 and 10 kD, respectively, by SDS gel electrophoresis (silver stain) and has been purified through the use of immobilized human anti-RNP immunoglobulin. Scl-70 antigen has one major band at 68 kD by SDS gel electrophoresis (silver stain) and has been purified through the use of immobilized human anti-Scl-70 immunoglobulins. Jo-1 antigen has one major band at 50 kD by SDS gel electrophoresis (silver stain) and has been purified through the use of immobilized human anti-Jo-1 immunoglobulins. dsDNA double-stranded (native) deoxyribonucleic acid, ssDNA single-stranded DNA, whole Histones, Histone subclasses (distinct molecular fractions) tissue extracts, human antibodies, animal tissue acetone powders, sera and immunoglobulin fractions, second antibodies, anti-whole sera, whole antisera to animal proteins and to human proteins have been used in enzyme immunoassay (ELISA) for detecting or evaluating systemic rheumatic diseases. Immunovision, Inc. of Springdale, Ark. has developed a number of enzyme-linked immunoassays, ouchterlony immunoprecipitation assays, and Western blot assays for detecting human antibody to particular nuclear antigens (ENA).

The presence of human autoantibodies to nuclear antigens, for example, antibodies against RNP/Sm, Sm, SS-A, SS-B, and Scl-70 antigens have been diagnostic when evaluating patients with Systemic Lupus Erythematosis (SLE). Positivity may indicate more progressive disease states or simply rheumatoid arthritis. Currently, enzyme linked immunosorbent assay (ELISA) has been the assay of choice to detect these antibodies. Antibodies to Smith (Sm) antigen have been shown to occur in twenty-five to thirty percent of patients with Systemic Lupus Erythematosis. Antibodies to Sm are less commonly found in patients with other rheumatic diseases. Antibodies to ribosomal nuclear protein (nRNP) have been found in patients with Systemic Lupus Erythematosis. They are also found in sera from patients with rheumatoid arthritis, Sjogren's Syndrome (SS), Progressive Systemic Sclerosis (PSS), and Mixed Connective Tissue Disease (MCTD). Twenty to thirty percent of the patients with antibodies to Scl-70 antigen have Progressive Systemic Sclerosis. Antibodies to Scl-70 are rarely found in patients with other systemic rheumatic diseases. Antibodies to Ro (SS-A) antigen are found in half of Systemic Lupus Erythematosis patients, most patients with Sjogren's Syndrome or Subacute Lupus Erythematosis and nearly all mothers of infants with congenital complete heart block or Neonatal Lupus Dermatitis. Antibodies to the La (SS-B) antigen usually occur in twenty to thirty percent of Sjogren's Syndrome patients and with five to ten percent of Systemic Lupus Erythamatosis patients. Antibodies to Jo-1 antigen are usually found in patients with polymyositis. Antibodies to Ribosomal P antigens are found to occur in five to ten percent of Systemic Lupus Erythematosis patients and ninety percent of those patients will demonstrate signs of lupus psychosis. Antibodies to mitochondrial antigens are found in all primary biliary cirrhosis patients. Antibodies to histone antigens (H1, H2A, H2B, H3, H4) are found in ninety-five to one-hundred percent of drug-induced Lupus Erythematosis, fifteen to twenty percent rheumatoid arthritis, and thirty percent of all patients with Systemic Lupus Erythematosis. Antibodies to cytoplasmic components of neutrophil granulocytes are present in the serum of patients with acute Wegener's granulomatosis and microscopic polyarteritis. Myeloperoxidase and proteinase 3 are the two major antigens present.

Tan and Peebles (37) in the Manual of Clinical Immunology describe a hemagglutination technique to quantitate antibodies to Sm and RNP. Durata and Tan (4), using saline-soluble extracts (ENA) from rabbit thymus acetone powder at a concentration of 5 mg protein/mL, demonstrated that increased sensitivity for detecting precipitating antibodies to RNP, Sm, and SS-B could be obtained by using CIE. A modified Ouchterlony technique has been used to show precipitating antibodies to RNA (35). Immunovision, Inc. has modified and tested the standard procedure (14) for enzyme immunoassays for the detection of autoantibodies using purified antigens.

There are many applications in the field of immunological monitoring in which the presence of body fluid antibodies and antigens are detected by a variety of methods. However, these assays usually measure one antibody or antigen at a time and tend to be time consuming and costly. Latex particles are commonly used clinically for detecting antibodies with agglutination as the end point. U.S. Pat. No. 5,162,863 discloses a method using flow cytometry to detect multiple antigens or antibodies with agglutination of particles combined with light scatter as the end point.

Microsphere based assays using flow cytometry have been reported by several investigators (20, 8) after Horan et al. reported the use of polystyrene microspheres to detect serum rheumatoid factor in 1979 (13).

The merger of bead assays with flow cytometry has been demonstrated in several clinical applications, e.g. detection of antibodies to CMV and herpes simplex (19); detection of antibodies to different components of the human immunodeficiency virus (HIV) (29); detection of antibodies to several antigens of *Candida albicans* (23); detection of human anti-mouse antibody (HAMA) in transplant patients receiving OKT3 (16); detection of circulating immune complexes (22) and HIV antibody in immune complexes (21); and detection of two different antibodies to CEA (17).

Although interest has focused on the detection of antibodies and antigens in fluids, the use of other ligand systems and biological probes has been explored, e.g. competitive binding of antibiotics to DNA coated beads (28) and detection of viruses (40).

Although the principals and advantages of fluorescent microsphere immunoassays have been discussed in the literature, applications in clinical lab testing have been relatively few despite the economics of time and cost inherent in this technology.

Current assays for the auto-antibodies seen in several autoimmune disorders are performed individually and require a separate kit for each antibody A method that will simultaneously assay for several different antibodies in one tube would be of significant value.

Hence, there is a need for an improved immunoassay method and apparatus for detecting and quantifying autoantibodies to nuclear antigens associated with autoimmune diseases as well as for detecting other antigens, antibodies, cell fragments, and the like.

SUMMARY OF THE INVENTION

In accordance with the present invention, immunoassay methods and apparatus are provided which utilize flow cytometry, coated latex microspheres, and fluorochrome labelled antibodies, to simultaneously detect the presence and amount of several antigens or antibodies in a sample.

The use of microspheres, beads, or other particles as solid supports for antigen-antibody reactions in order to detect antigens or antibodies in serum and other body fluids is particularly attractive when linked to flow cytometry. Flow cytometers have the capacity to detect particle size differences and are highly sensitive fluorescence detectors.

Microspheres can be sized by forward angle light scatter (FALS) or electronic volume. Used in conjunction with right angle light scatter (RALS), a flow cytometer (FCM) can distinguish between single and aggregated particles. By combining FALS and fluorescence, it is practical to use beads of several different sizes, each bead coated with a different protein, for the simultaneous detection of multiple analytes (antigens or antibodies). Microspheres can be coated with proteins passively or covalently depending on their chemical makeup.

The strengths of this type of assay are: 1) the ability to simultaneously, but discretely, analyze multiple analytes; 2) the simplicity of binding proteins to microspheres; 3) the ability of flow cytometry (FCM) to detect small particle size differences; and 4) the exquisite sensitivity of FCM as a detector of different wavelengths of fluorescence, simultaneously. Available auto-sampling systems make it even more appealing in this regard. The capacity to simultaneously detect multiple analytes in one tube in a immunoassay system suggests that immunoassays and biological probe assays may ultimately mimic multichannel chemistry analyzers with all of their benefits.

In accordance with one embodiment of the present invention, highly purified RNP, Sm, SS-A, SS-B and Scl-70 antigens are bound to 4, 5, 6, 7 and 10 $\mu$m latex beads, respectively and stabilized for extended shelf life. Diluted patient serum is placed into test tubes containing a mixture of five antigen coated beads and incubated. If an antibody is present for a specific antigen, it will bind to that specific bead. After washing the bead/serum mixture to remove residual sample, a second incubation with goat anti-human IgG, conjugated with a fluorochrome such as fluorescein isothiocyanate (FITC), is carried out. This conjugate will bind immunologically to the anti-antigen IgG of the antigen-antibody complex, forming a "sandwich" consisting of bead—antigen—1° (primary) antibody—2° (secondary) antibody—FITC (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers (PMTS) which convert the fluorescent analog signals into two parameter histograms expressing forward light scatter (Y-axis) versus fluorescence intensity (X-axis, FIG. 2).

In accordance with another embodiment of the invention, a fluorescent immuno-bead assay (FIBA) kit is used in conjunction with flow cytometry (FCM) for the simultaneous detection of the antinuclear antibodies to RNP (ribonucleo-protein) seen in mixed connective tissue disease, systemic lupus erythematosis (SLE), Sjogren's syndrome, scleroderma and polymyositis; Sm (Smith antigen) in SLE; SS-A in Sjogren's syndrome and SLE; SS-B in Sjogren's syndrome and SLE; and Scl-70 in scleroderma. These antibodies are commonly encountered in the so-called rheumatic diseases.

By attaching each of these antigens to different sized latex beads, the presence of antibodies to one or more of these antigens can be rapidly detected and semi-quantitated. Instead of the five or more separate assays currently required, one assay involving five or more beads of different sizes in one tube provides the information needed. The cost saving in terms of materials, supplies, and technician time are estimated to be 60–70%. This can be further enhanced by utilizing robotic auto-sampling devices currently available or being developed for flow cytometry, for example, the Ortho Diagnostic Systems CytoronAbsolute with an auto-biosampler.

The principal object of the present invention is the provision of an immunobead-flow cytometry assay for simultaneously detecting a plurality of antigens or antibodies in a sample.

Another object of the present invention is the provision of a multiple parameter latex bead suspension and flow cytometry to simultaneously detect the presence of a plurality of autoantibodies to nuclear antigens associated with autoimmune disease A still further object of the present invention is the provision of a double wash fluorescent immunobead assay.

Yet another object of the present invention is the provision of a no-wash fluorescent immunobead assay.

Another more particular object of the present invention is a commercial assay kit designed to simultaneously detect several anti-nuclear antibodies in patient sera utilizing antigen coated microspheres of different sizes. Binding of antibody to spheres is detected by FITC labelled anti-human IgG and flow cytometry. Each individual antibody is detected because of binding to a different sized sphere which is determined by light scatter.

Future applications are essentially unlimited because the immunoassay of the present invention can be applied to any ligand binding system and the number of simultaneous assays can be expanded by the use of combinations of fluorophores and multiple microsphere sizes.

Other objects and further scope of the applicability of the present invention will become apparent from the detailed description to follow, taken in conjunction with the accompanying drawings wherein like parts are designated by like reference numerals.

DETAILED DESCRIPTION OF THE PREFERRED EMBODIMENTS

In accordance with an exemplary embodiment of the present invention, antigen coated latex surfaces, anti-nuclear antibodies, fluorescenated antibodies against such anti-nuclear antibodies, and flow cytometry are combined to provide multiparameter devices for the detection of a plurality of antigens in a single tube.

Figure 1:
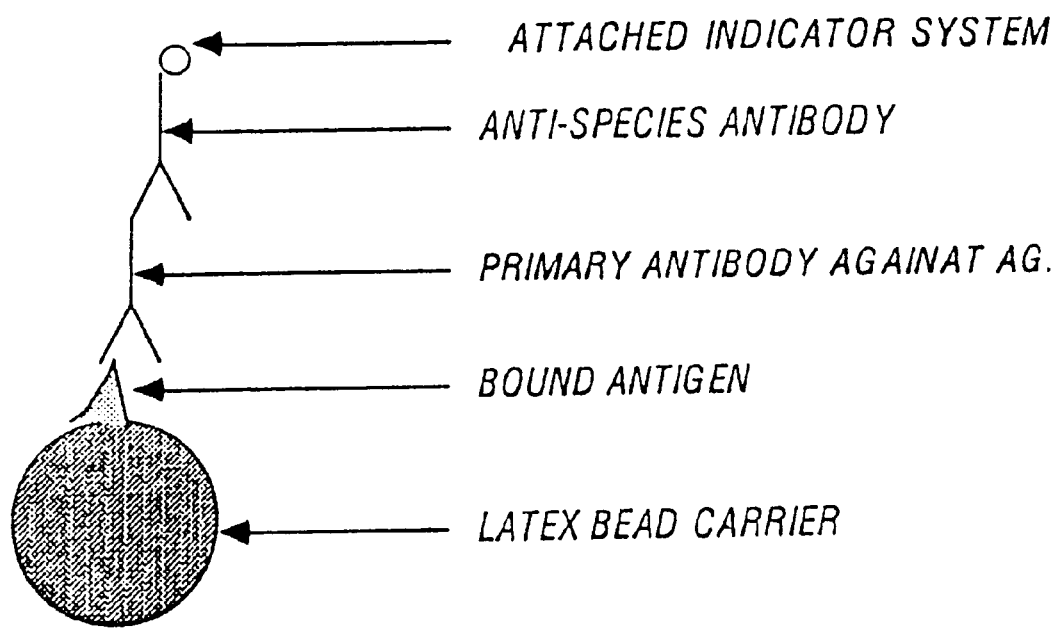
FIG. 1 is a schematic representation of an exemplary immunological structure of the bead-antigen-antibody indicator complex.

One basic principle of the present invention is to conjugate antigens or antibodies to the exterior of latex microspheres (beads) of different sizes. The coated microspheres are used to detect the appropriate specific antibodies or antigens simultaneously in one tube. The ability to detect multiple analytes in one reaction tube eliminates the variability often seen in results arising from separate assays. Procedurally, latex beads are coated with specific antigens or antibodies. These beads vary in size and may also contain or be impregnated with fluorescent dyes e.g. FITC, PE, etc. One or more of these precoated beads are then incubated with the sample (serum, body fluid) solution. If an antibody-antigen complex has been formed, a 2° (secondary) indicator fluorochrome labelled antibody will bind to the appropriate bead (FIG. 1).

Figure 2:
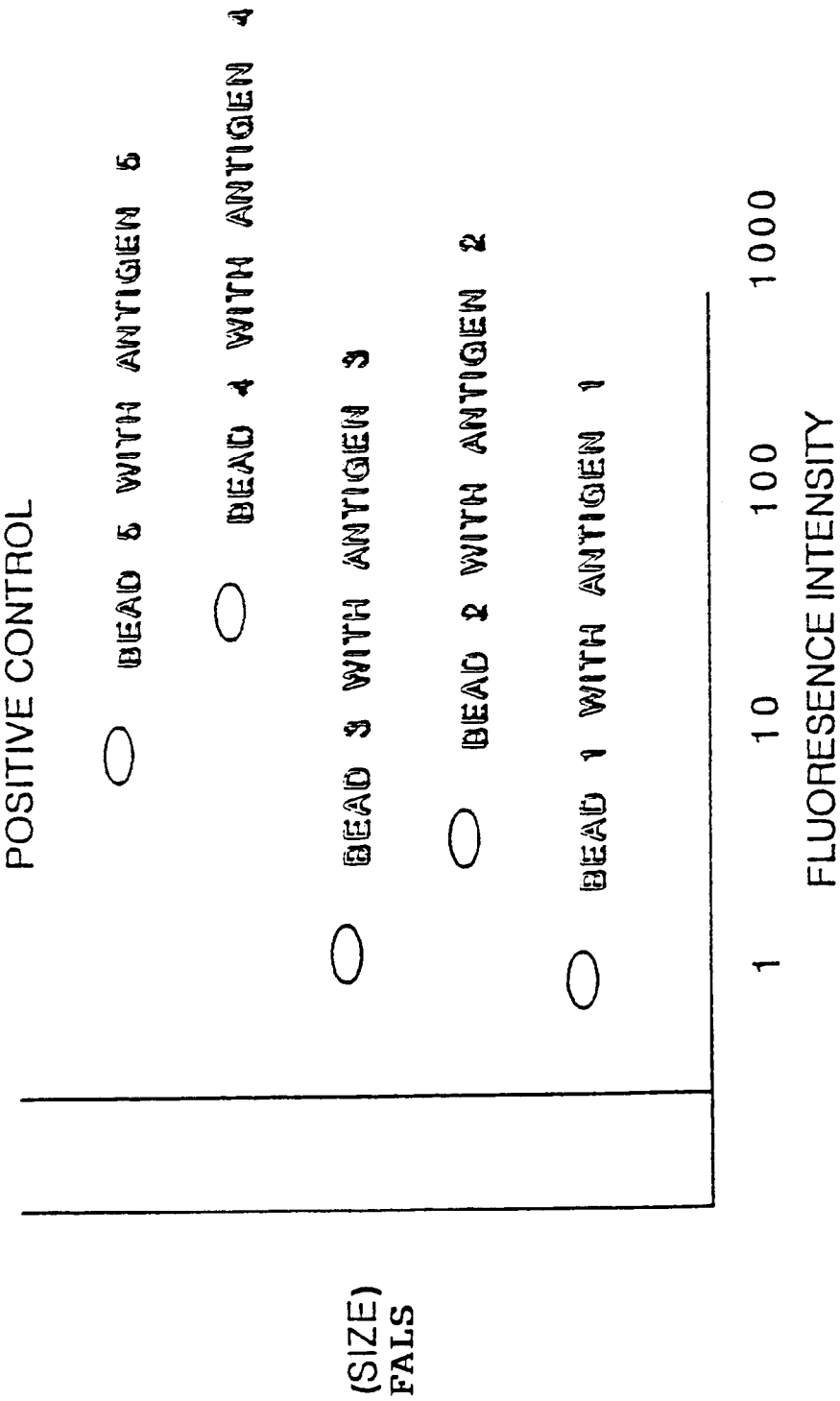
FIG. 2 is a schematic illustration of the flow cytometer histogram of forward angle light scatter (size) versus fluorescence on a positive control sample in a multiple bead system.
Figure 3:
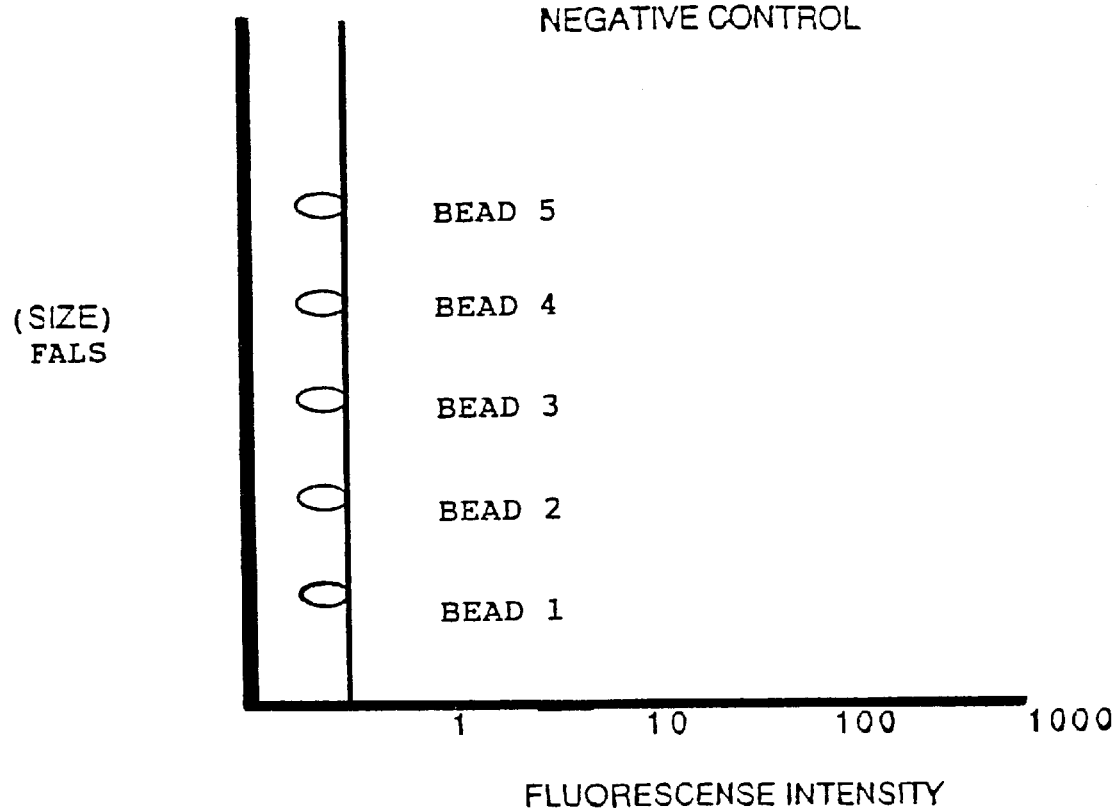
FIG. 3 is a schematic representation of a flow cytometer histogram of a negative control in a multiple bead system.

The beads are centrifuged, washed, and analyzed using forward angle light scatter to discriminate the different sized beads, each bound to a different antigen or antibody, and analyzed to detect fluorescence with a flow cytometer. The solution containing beads is passed through a series of tubes until it reaches the optical quartz cell of the flow cytometer. Because of the laminar flow of sheath fluid, single particle analysis is achieved. The signal is converted from analog to a digital display representing the size of the spheres and fluorescence of each (FIG. 2). Controls are used to adjust for the fluorescence background created by electronic and particle noise (FIG. 3). A forward scatter (size) adjustment of the multiple sized bead antigen or antibody complexes is necessary in order to semi-quantitate or quantitate the relative concentration of antigen or antibody on the bead surface through single screen, visual distribution. As seen in FIG. 3, a fluorescent threshold (x-axis) is established below which fluorescence values are considered negative. Upon addition of a "positive" sample, (containing appropriate antibody or antigen), the reaction between the fluorochrome labelled indicator antibody and antigen or antibody bead complex, amplifies the fluorescence signals detected by the flow cytometer (FIG. 2). Thus, the definition of "positivity" in this system is relative to the negative control (background) and can easily be interpreted.

Figure 4:
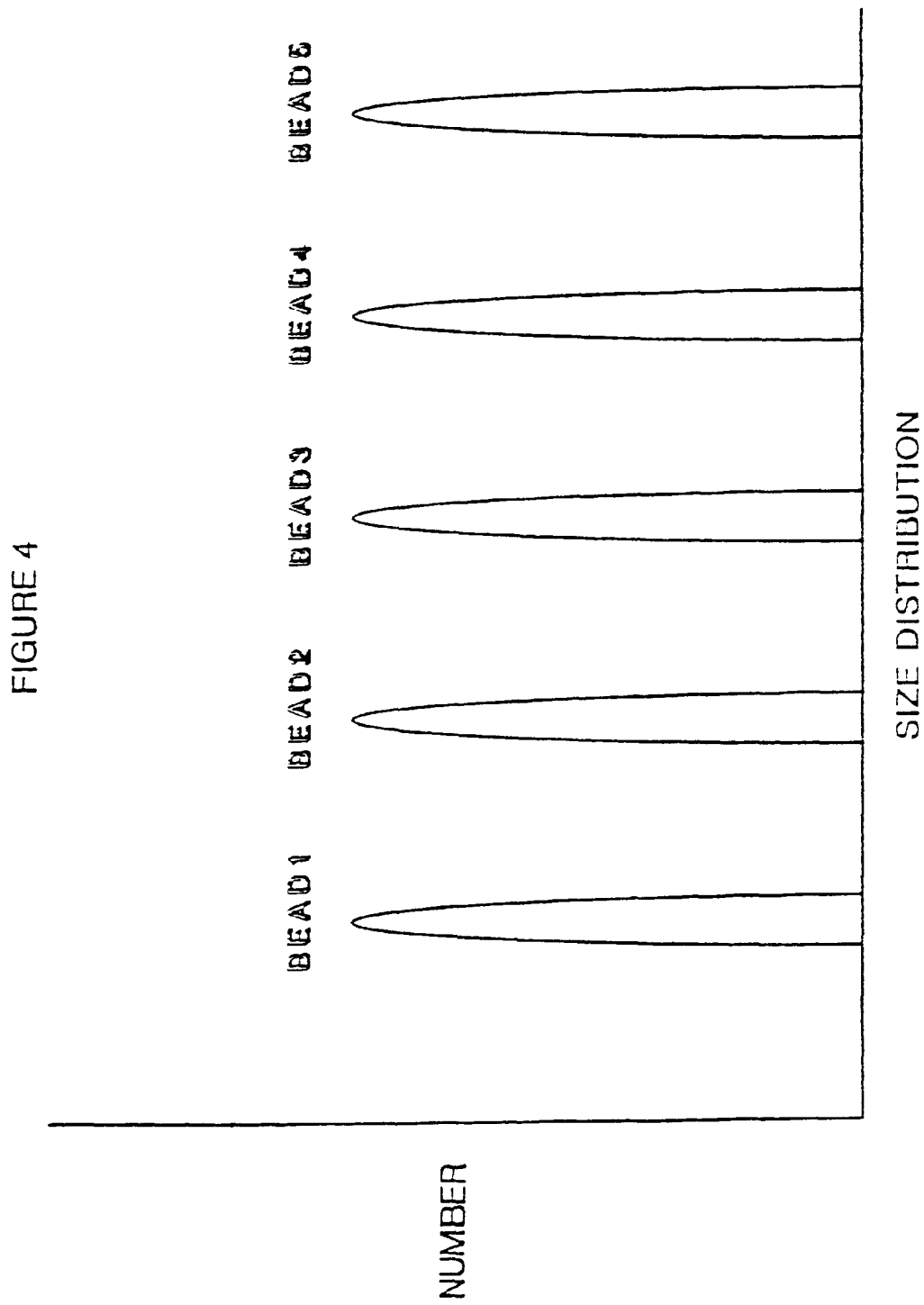
FIG. 4 is a schematic illustration of a flow cytometer histogram of the size characteristics of latex beads when run on a flow cytometer.

Multiple antibodies or antigens can readily be displayed and quantitative values obtained in a single two-dimensional histogram. Similarly, additional bead systems can be combined within the size distinguishing capabilities of the flow cytometer and the sizes available from vendors providing latex particles (FIG. 4). As seen in FIG. 1, the multiple antigen or antibody coated bead system incorporates specific anti-species specific 2° (secondary) antibodies, labelled with fluorochromes (e.g., FITC, PE), to detect the presence of antigen-antibody complexes on the beads. All other antibodies non-specifically bound to the latex surface are either washed away or ignored by the indicator antibody.

The present invention uses the principles of flow cytometry and light scatter to detect different sizes of latex particles with fluorescence as the endpoint. Multiple antigens or antibodies in body fluids are detected simultaneously in a single tube because each specific antibody or antigen is differentiated by the size of the bead it is bound to. This invention differs from the procedure disclose in U.S. Pat. No. 5,162,863 in that the latter "measures the presence of the amount of a plurality of kinds of particular antigens or antibodies in a specimen at a time by a simple construction without the use of fluorescence" and "it has been difficult to reliably discriminate between kinds of the particles from the fluorescence."

Advantages of the present invention include:

1. Because of varying sizes and dyes of microspheres, multiple antibodies or antigens can be detected and quantitated simultaneously in a single tube.

2. Specific antibodies/antigens can much more easily be detected when bound to latex bead surfaces due to the separation0 of one antigen/antibody from the other.
3. Because of the sensitivity of fluorescence based flow cytometry this assay tends to be capable of detecting lower levels of antibodies/antigens than other conventional assay methods e.g. EIA, ELISA, agglutination etc.
4. Because of a relatively unlimited range of bead sizes, other bead physical characteristics, fluorochromes and probes this invention offers great flexibility.
5. Single tube analysis facilitates the utilization of "batch-mode" processing and automation.
6. The present assay system can be used in screening, semi-quantitative or quantitative methods.
7. Almost any flow cytometer may be utilized for this method.
8. Minimal volumes of sample are necessary in order to run multiple assays.
9. Materials bound to the latex bead surface may be antigens, antibodies, chemicals, microorganisms, cell components, and other substances capable of binding specifically to an appropriate ligand, including DNA and RNA for in situ hybridization.

EXAMPLE 1

Double Wash Detection System

In accordance with one example of the present invention, five distinct latex beads coated with a unique antigen are incubated with diluted human serum and then labelled with goat anti-human FITC labelled antibodies. Positivity is distinguished or semi-quantitated using a blank or isotypic control as the negative standard. Forward scatter (forward angle light scatter, FALS, size) versus green fluorescence are used to detect positivity.

Purified antigens, positive control sera, human antibodies, monospecific donor plasma, anti-human antibodies, etc. for autoimmune testing are commercially available. For example, ImmunoVision, Inc. of Springdale, Ark. produces affinity purified, highly immunospecific, antigens such as Ro(SS-A), La(SS-B), Sm(Smith), Sm/RNP, Scl-70, and Jo-1 as well as purified whole histones and histone subclasses (distinct molecular fractions). ImmunoVision, Inc. also provides positive control sera for autoimmune testing, human antibodies against Ro(SS-A), La(SS-B), Sm, RNP, Scl-70, Jo-1, PM-1, monospecific donor plasma against Cardiolipin, dsDNA, Jo-1, Mitochondrial, PCNA, PM-1, Po, RNP, Scl-70, Sm, Ro(SS-A), La(SS-B), and thyroid microsomal, animal tissue acetone powders, animal sera and immunoglobulin fractions (whole serum, gamma fractions, purified IgG), animal second antibodies (whole antisera, IgG fractions, affinity purified), anti-whole sera, mouse antisera, and whole antisera to selected animal and human proteins.

Materials

4 $\mu$m particle sized latex bead, Duke Scientific, Cat #4204A

5 $\mu$m particle sized latex bead, Duke Scientific, Cat #4205A

6 $\mu$m particle sized latex bead, Duke Scientific, Cat #4206A

7 $\mu$m particle sized latex bead, Duke Scientific, Cat #4207A

10 $\mu$m particle sized latex bead, Duke Scientific, Cat #42i0A

Sm/RNP Complex antigen, Immunovision, Cat #SCR-3000

Sm antigen, 1000 units, Immunovision, Cat #SMA-3000

SS-A (Ro) antigen, 1000 units, Immunovision, Cat #SSA-3000

SS-B (La) antigen, 1000 units, Immunovision, Cat #SSB-3000

Scl-70 antigen, 1000 units, Immunovision, Cat # SCL-3000

Anti-RNP, lyophilyzed, Immunovision, Cat # HRN-0100

Anti-Sm, lyophilyzed, Immunovision, Cat # HSM-0100

Anti-SS-A (Ro) lyophilyzed, Immunovision, Cat # HSA-0100

Anti-SSB (La), lyophilyzed, Immunovision, Cat # HSC-0100

Anti-Scl-70, lyophilyzed, Immunovision, Cat # HSC-0100

Goat anti-human IgG F(ab')$_2$-FITC, Tago, Inc., Cat #4200

Sodium Carbonate, Sigma Chemical, Cat # S-6139

Sodium Bicarbonate, Baker Chemical, Cat # 3506-1

Albumin, bovine, Sigma Chemical, Cat # A-7888

200 $\mu$L adjustable pipettor pipettor tips 10 mL pipettes

Centrifuge

12×75 mL polystyrene test tubes 13 mm caps flow cytometer

Reagents

Carbonate Buffer, pH 9.6

1. Add 1.5 g of sodium carbonate and 0.8 g of sodium bicarbonate to 500 mL of distilled water.
2. Mix for 5–10 minutes or until all crystals are dissolved.
3. Adjust pH to 9.6 using 2N NaOH.
4. Store at 4–8° C.
5. Buffer only to be used for less than 48 hours after preparation. For antigen coating only.

0.5% albumin, bovine in PBS

1. Mix 0.5 g of bovine albumin in 100 mL of PBS.
2. Mix thoroughly.
3. Store at 4–8° C. for one month.

Procedure

1. Determine the amount of latex bead suspension (e.g. # of drop w/mL carbonate buffer) needed to achieve an event count of 900–1000 beads/second on the flow cytometer.
2. Titer antigen (Ag) to appropriate $\mu$g/mL and use concentration deemed optimal for maximum mean channel and fluorescence.
3. Add antigen to each respective tube: ($\mu$g)

| Anitigen (size bead) | Drops/mL Buffer | Ag/mL Buffer |
|---|---|---|
| RNP (4 $\mu$m) | 3 | 30 |
| Sm (5 $\mu$m) | 3 | 10 |
| SS-A (6 $\mu$m) | 6 | 15 |
| SS-B (7 $\mu$m) | 6 | 15 |
| Scl-70 (10 $\mu$m) | 10 | 10 |

4. Incubate bead/antigen mixture for 12–18 hours at 4–8° C.
5. Centrifuge solution at full speed in a refrigerated centrifuge for 10 minutes.

6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Dilute positive, negative and patient serum 1:20 in PBS.
13. Add 50 µL of each serum diluted to appropriately labelled tube.
14. Vortex gently and incubate for 15 minutes at room temperature.
15. Wash once with 1 mL carbonate buffer.
16. Repeat steps 5 and 6.
17. Add 20 µL of Goat anti-human IgG F(ab')$^2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 2

Double Wash Detection System

In accordance with another example of the present invention, an immunobead-flow cytometry method for simultaneously detecting a plurality of antigens is as follows.

Procedure

1. Determine the amount of latex bead suspension (e.g. # of drop w/mL carbonate buffer) needed to achieve an event count of at least 500 beads/second on the flow cytometers.
2. Titer antigen (Ag) to appropriate µg/mL and use concentration deemed optimal for maximum mean channel and fluorescence.
3. Add antigen to each respective tube: (µg)

| Antigen (size bead) | Drops/mL Buffer | Ag/mL Buffer |
|---|---|---|
| RNP (0.25 µm) | 3 | 30 |
| Sm (0.50 µm) | 3 | 10 |
| SS-A (0.75 µm) | 6 | 15 |
| SS-B (1.0 µm) | 6 | 15 |
| Scl-70 (1.25 µm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Add 500 µL of the 5 antigen-coated bead suspension
13. Add 50 µL of a 1:20 dilution of patient or control serum diluted in saline.
14. Gently vortex and incubate for 15 minutes at room temperature.
15. Make a 1:5 dilution of Goat anti-human F(ab')$^2$ IgG—FITC in 0.5% albumin solution in PBS.
16. Add 50 µL of diluted conjugate to the bead suspension.
17. Incubate for 15 minutes at room temperature in the dark.
18. Add 1 mL of PBS.
19. Analyze on flow cytometer.

Cytometer adjustments of fluorescent gains will change, therefore, it is recommended that a blank and normal control be run as reference material. Conjugate titers may vary, serial dilutions must be made on all new lots.

EXAMPLE 3

Double Wash Detection System

In accordance with yet another example of the assay of the present invention the method follows.

Procedure

1. Determine the amount of latex bead suspension (e.g. # of drop w/mL carbonate buffer) needed to achieve an event count of 900–1000 beads/second on the flow cytometer.
2. Titer antigen (Ag) to appropriate µg/mL and use concentration deemed optimal for maximum mean channel and fluorescence.
3. Add antigen to each respective tube: (µg)

| Antigen (size bead) | Drops/mL Buffer | Ag/mL Buffer |
|---|---|---|
| RNP (660 µm) | 3 | 30 |
| Sm (680 µm) | 3 | 10 |
| SS-A (700 µm) | 6 | 15 |
| SS-B (720 µm) | 6 | 15 |
| Scl-70 (740 µm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Dilute positive, negative and patient serum 1:20 in PBS.
13. Add 50 µL of each serum diluted to appropriately labelled tube.
14. Vortex gently and incubate for 15 minutes at room temperature.

15. Wash once with 1 mL carbonate buffer.
16. Repeat steps 5 and 6.
17. Add 20 μL of Goat anti-human IgG F(ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 4
Double Wash Detection System

In accordance with still another example of the present invention the assay is as follows.
Procedure
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add antigen to each respective tube: (μg)

| Antigen (size bead) | Drops/mL Buffer | Ag/mL Buffer |
|---|---|---|
| Sm/RNP (4 μm) | 3 | 30 |
| Jo-1 (5 μm) | 3 | 10 |
| Ro/SS-A (6 μm) | 6 | 15 |
| La/SS-B (7 μm) | 6 | 15 |
| dsDNA (10 μm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Dilute positive, negative and patient serum 1:20 in PBS.
13. Add 50 μL of each serum diluted to appropriately labelled tube.
14. Vortex gently and incubate for 15 minutes at room temperature.
15. Wash once with 1 mL carbonate buffer.
16. Repeat steps 5 and 6.
17. Add 20 μL of Goat anti-human IgG F(ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 5
Double Wash Detection System

In accordance with another example of the present invention the multiple parameter bead assay is as follows.
Procedure
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add antigen to each respective tube: (μg)

| Antigen (size bead) | Drops/mL Buffer | Ag/mL Buffer |
|---|---|---|
| ss-DNA (4 μm) | 3 | 30 |
| Ribosomal P (5 μm) | 3 | 10 |
| Mitochondria (6 μm) | 6 | 15 |
| Histone H1 (7 μm) | 6 | 15 |
| Histone H2A (10 μm) | 10 | 10 |

4. Incubate bead/antigen mixture for 12–18 hours at 4–80C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Dilute positive, negative and patient serum 1:20 in PBS.
13. Add 50 μL of each serum diluted to appropriately labelled tube.
14. Vortex gently and incubate for 15 minutes at room temperature
15. Wash once with 1 mL carbonate buffer.
16. Repeat steps 5 and 6.
17. Add 20 μL of Goat anti-human IgG F(ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

Figure 5:
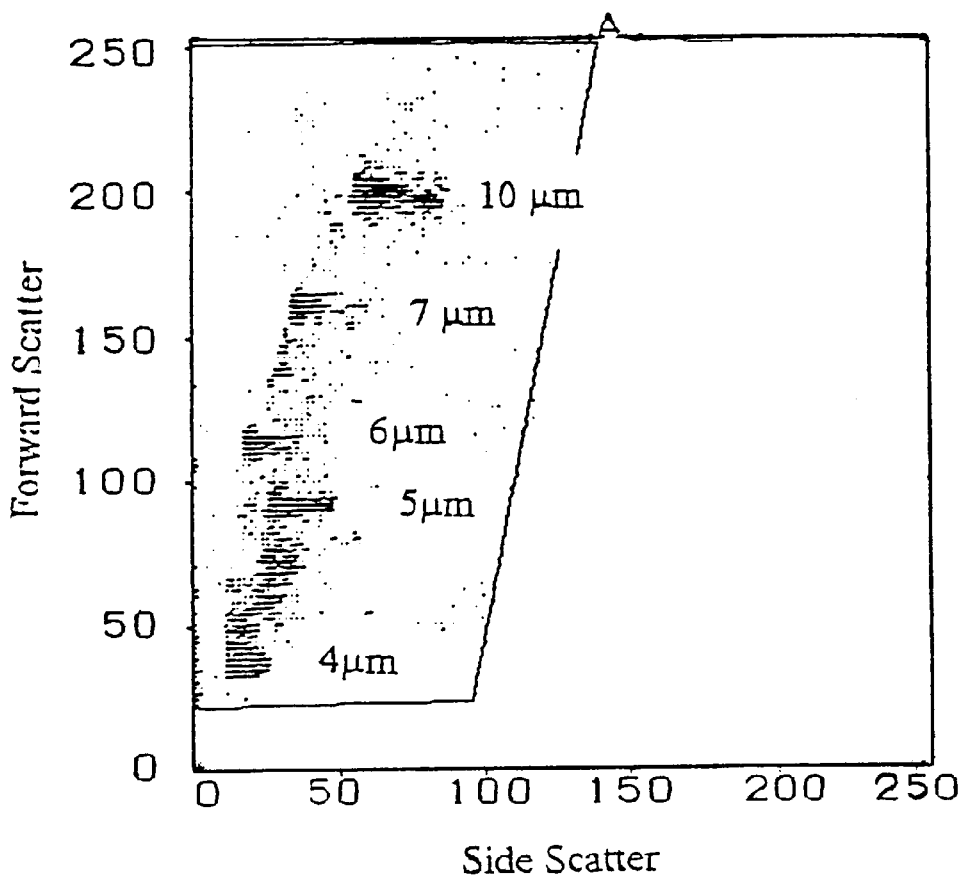
FIG. 5 is a representation of a flow cytometer cytogram of the size and complexity distribution as is seen with a patient sample of beads coated with antigen and analyzed in a flow cytometer.

It has been demonstrated that the antigens, RNP, Sm, SS-A, SS-B, and Scl-70, can be attached to latex beads of the following sizes, 4, 5, 6, 7, and 10 μm, respectively (FIG. 5). After incubation with sera from patients with antibodies to these antigens, followed by the addition of fluorescenated anti-human IgG, beads that have bound antibody fluoresce and are specifically detectable because of their size differences (FIGS. 1, 2, 6, & 7).

The results of the assays of the present invention are improved by determining: 1) optimal concentrations of antigens on latex microspheres using block titration methods; 2) optimal ratios of serum to bead concentrations; and 3) optimal concentrations of secondary antibody (anti-human IgG). Once optimal antigen-bead-antibody concentrations are determined and, using commercially available human sera containing these antibodies, antigen coated beads are incubated with various dilutions of sera and secondary (detector) antibody. Several dilutions of known positive sera are performed to determine the sensitivity of the assay.

Following these baseline studies, the FIBA-FCM assay of the present invention is tested in parallel with ELISA kits for detection of these antibodies. It is preferred that 40–50 healthy blood donors and 250–300 patient samples be assayed with ELISA kits, one kit for each antibody, in parallel with the present FIBA assay for all of the antibodies in one tube. Also, 15–20 patient and healthy donor samples should be assayed by the present FIBA-FCM on three different flow cytometers, for example, Cytoron Absolute (Ortho Diagnostic), FACScan (Becton-Dickinson), and Profile II (Coulter), to determine if the assay is subject to instrument variation.

Further, replicates should be performed on an automated system, e.g. the Cyotoron Absolute with an auto-sampler, to determine reproducibility. Stability of antigen coated beads is determined by a longitudinal study in which beads are tested for their reactivity to the same sera at monthly intervals for at least six months.

Each FIBA-FCM assay kit of the present invention should be tested in multiple clinical flow cytometry laboratories, using the same positive and negative sera to determine inter-laboratory variation.

Figure 8:
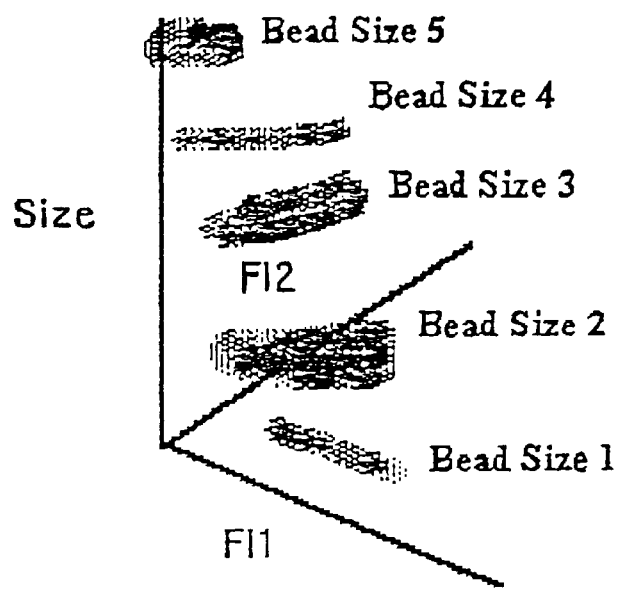
FIG. 8 is an illustration of a three dimensional flow cytometer histogram of the three parameters of bead size, first fluorescence color (Fl1), and second fluorescence color (Fl2)
Figure 9:
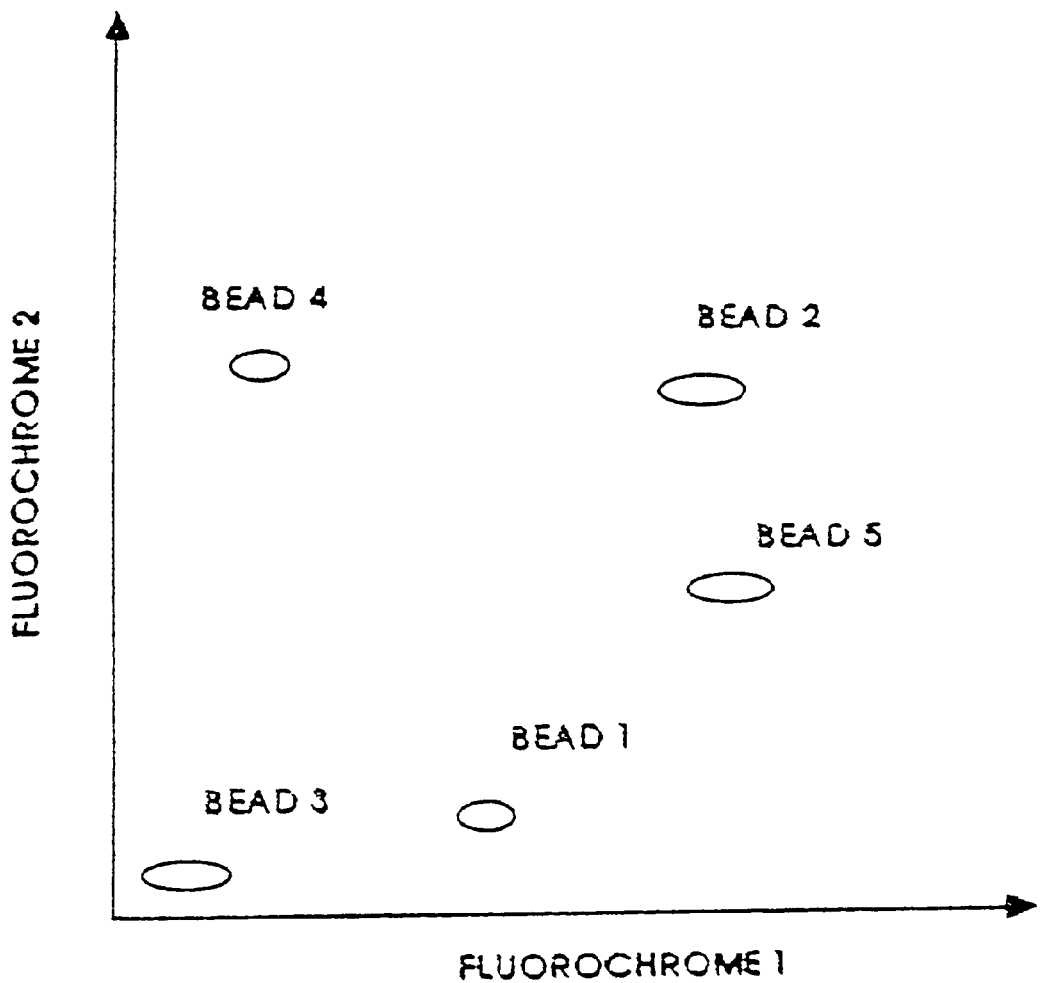
FIG. 9 is a schematic representation of a two dimensional flow cytometer histogram of different sized beads labelled with different fluorochromes.

The methodology of the present invention provides that microsphere sizes are combined with two color FCM and results displayed three dimensionally as a "cloud" display (FIG. 8). This increases the number of antibodies or antigens to be simultaneously analyzed (FIG. 9).

EXAMPLE 6
Multiple Parameter Detection System

In accordance with another embodiment of the present invention, highly purified RNP, Sm, SS-A, SS-B and Scl-70 antigens are bound to 4, 5, 6, 7 and 10 $\mu$m latex beads, respectively and stabilized for extended shelf life. Diluted patient serum is placed into test tubes containing a mixture of the five antigen coated beads and incubated. If an antibody is present for a specific antigen, it will bind to that specific bead. After washing the bead/serum mixture to remove residual sample, a second incubation with goat anti-human IgG, conjugated with fluorescein isothiocyanate (FITC), is carried out. This conjugate will bind immunologically to the anti-antigen IgG of the antigen-antibody complex, forming a "sandwich" consisting of bead—antigen—1° antibody—2° antibody—FITC (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into two parameter histograms expressing forward light scatter (Y-axis) versus fluorescence intensity (X-axis, FIG. 2).

Procedure
1. Determine which antigen coating buffer (either carbonate buffer or phosphate buffered saline, PBS) yields highest binding capacity to latex beads. Optimal concentration of beads needs to be determined in order for the flow cytometer to count accurately.
2. Establish titers of both antibody against the coated beads and run several experiments to maximize signals obtained at different antigen concentrations (mean channel fluorescence).
3. Incubate antigen/serum mixture for several minutes (time to be determined) and wash with either carbonate buffer or PBS.
4. Wash antigen coated beads in buffer (PBS or 0.5% Tween 20 in PBS or carbonate buffer).
5. Determine the background of unlabelled beads.
6. If background exists, decrease to near baseline values.
7. Find proper dilution of patient and control sera and add to coated beads.
8. Incubate for optimal time (to be determined) and wash with buffer (PBS or carbonate buffer).
9. Determine the optimum amount of a labelled goat-anti-human F(ab')$^2$ antibody by titration and use as the indicator system.
10. Repeat step 8.
11. Add 1 mL of buffer (PBS or carbonate buffer).
12. Read on flow cytometer.

Quality Control

Negative and positive controls are included in each assay During development all patient samples are tested in parallel by a conventional ELISA method. Reagents are used only during established shelf-lives.

Limitations

Hemolyzed or lipemic samples may affect assay.

Human Subjects

Sera previously obtained for other purposes and frozen as archival material.

EXAMPLE 7
Multiple Parameter Detection System

In accordance with one embodiment of the present invention highly purified RNP, Sm, SS-A, SS-B and Scl-70 antigens are bound to 1, 25, 50, 75 and 100 $\mu$m latex beads, respectively and stabilized for extended shelf life. Diluted patient serum is placed into test tubes containing a mixture of the five antigen coated beads and incubated. If an antibody is present for a specific antigen, it will bind to that specific bead. After washing the bead/serum mixture to remove residual sample, a second incubation with anti-human IgG, conjugated with fluorescein isothiocyanate (FITC), is carried out. This conjugate will bind immunologically to the anti-antigen IgG of the antigen-antibody complex, forming a "sandwich" consisting of bead—antigen—1° antibody—2° antibody—FITC (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into at least two parameter histograms expressing forward light scatter (Y-axis) versus fluorescence intensity (X-axis FIG. 2).

Procedure:
1. Determine which antigen coating buffer (either carbonate buffer or phosphate buffered saline, PBS) yields highest binding capacity to latex beads. Optimal counts for beads need to be determined in order for the flow cytometer to count accurately.
2. Establish titers of both antibody against the coated beads and run several experiments to maximize signals obtained at different antigen concentrations (mean channel fluorescence).

3. Incubate antigen/serum mixture for several minutes (time to be determined) and wash with either carbonate buffer or PBS.
4. Wash antigen coated beads in buffer (PBS or 0.5% Tween 20 in PBS or carbonate buffer)
5. Determine the background of unlabelled beads.
6. If background exists, decrease to near baseline values.
7. Find proper dilution of patient and control sera and add to coated beads.
8. Incubate for optimal time (to be determined) and wash with buffer (PBS or carbonate buffer).
9. Determine the optimum amount of a labelled anti-human antibody by titration and use as the indicator system.
10. Repeat step 8.
11. Add 1 mL of buffer (PBS or carbonate buffer).
12. Read on flow cytometer.

Quality Control

Negative and positive controls should be included in each assay. During development all patient samples should be tested in parallel by a conventional ELISA method. Reagents should be used only during established shelf-lives.

Limitations

Hemolyzed or lipemic samples may affect assay.

Human Subjects

Sera may be previously obtained and frozen as archival material.

In accordance with another embodiment of the present invention, a "no wash" immunoassay, immunobead-flow cytometry highly purified RNP, Sm, SS-A, SS-B, and Scl-70 antigens are bound to 4, 5, 6, 7 and 10 μm latex beads, respectively and stabilized for extended shelf life. Diluted patient serum is placed into test tubes containing a mixture of five antigen coated beads and incubated. If an antibody is present for a specific antigen, it will bind to that specific bead. Next, a dilution of goat anti-human IgG-FITC in albumin in PBS is added and a second incubation is carried out. This conjugate will bind immunologically to the anti-antigen IgG of the antigen-antibody complex, forming a "sandwich" consisting of bead—antigen—1° antibody—2° antibody—FITC (FIG. 1). Then, PBS is added and the samples are analyzed on a flow cytometer.

EXAMPLE 8
One Step Bead Detection System
No Wash Detection System

The following "no wash" procedure is a modification of the above bead evaluation method and utilizes an albumin step in the conjugate to eliminate non-specific staining resulting from increased patient serum protein concentrations.

1. Allow reagents to come to room temperature.
2. Gently invert antigen coated bead mixture until an even distribution of bead product is observed.
3. Label test tubes for Blank, Controls, and Patients.
4. Add 500 μL of multiple bead suspension to each tube.
5. Dilute patient and control serum 1:20 in isotonic saline (e.g. 10 μL serum to 190 μL saline).
6. Add 50 μL of diluted serum to appropriate test tubes.
7. Add 50 μL of saline to blank tube.
8. Gently vortex and incubate for 15 minutes at room temperature.
9. Make a 1:5 dilution of goat anti-human F(ab')$_2$ IgG FITC (or other fluorochrome) in 0.5% albumin in PBS.
10. Add 50 μL of diluted conjugate to each tube.
11. Gently vortex and incubate for 15 minutes at room temperature, in the dark.
12. Add 1 mL of PBS to each tube.
13. Analyze on flow cytometer.

EXAMPLE 9
No Wash Detection System

1. Allow reagents to come to room temperature.
2. Gently invert antigen coated bead mixture until an even distribution of bead product is observed.
3. Label test tubes for Blank, Controls, and Patients.
4. Add at least 200 μL of bead suspension to each tube.
5. Dilute patient and control serum at least 1:10 in saline (e.g. 10 μL serum to 100 μL saline) 42
6. Add at least 10 μL of diluted serum to appropriate test tubes.
7. Add at least 10 μL of PBS to blank tube.
8. Gently vortex and incubate for at least 5 minutes at room temperature.
9. Make an at least 1:2 dilution of labelled anti-human antibodies in at least 0.2% albumin in PBS.
10. Add at least 10 μL of diluted conjugate to each tube.
11. Gently vortex and incubate for at least 5 minutes at room temperature, in the dark.
12. Add about 1 mL of PBS to each tube.
13. Analyze on flow cytometer.

EXAMPLE 10
No Wash Detection System

1. Allow reagents to come to room temperature.
2. Gently invert antigen coated bead mixture until an even distribution of bead product is observed.
3. Label test tubes for Blank, Controls, and Patients.
4. Add equal quantities of bead suspension to each tube.
5. Dilute patient and control serum to about 1:20 in saline (e.g. 10 μL serum to 190 μL saline).
6. Add equal quantities of diluted serum to appropriate test tubes.
7. Add the same quantity of PBS to blank tube.
8. Gently vortex and incubate at room temperature.
9. Make an about 1:5 dilution of labelled anti-human antibody in about 0.5% albumin in PBS.
10. Add equal quantities of diluted conjugate to each tube.
11. Gently vortex and incubate at room temperature.
12. Add equal quantities of PBS to each tube.
13. Analyze on flow cytometer.

EXAMPLE 11
Anti-SLE Screening Assay Test Kit

In accordance with still another embodiment of the present invention, an FIBA-FCM assay test kit is described as follows.

Summary of Procedure

1. Add 50 μL of sample to 500 μL of RNP, Sm, SS-A(Ro), SS-B(La), and Scl-70 coated bead solution. Mix well.
2. Incubate at room temperature for 15 minutes.
3. Add 1 μL PBS to each tube.
4. Centrifuge tubes for 10 minutes at 1500 g.

5. Decant supernatant and gently resuspend bead pellet.
6. Place one drop of fluorescenated conjugate into each tube. Mix well.
7. Incubate at room temperature, in the dark, for 15 minutes.
8. Add 1 μL PBS to each tube.
9. Centrifuge for 10 minutes at 1500 g.
10. Decant supernatant and gently resuspend bead pellet.
11. Add 1 μL of PBS.
12. Read on flow cytometer.

Intended Use of Kit

For the simultaneous detection of anti-antibodies to the antigens RNP, Sm, SS-A(Ro), SS-B(La), and Scl-70 in serum as an aid in the diagnosis and of certain so-called rheumatic or connective tissue diseases, e.g. systemic lupus erythematosis (SLE), Sjogren's syndrome, scleroderma, and polymyositis. For in vitro Diagnostic Use.

Summary and Explanation

Current approaches to the detection of auto-antibodies in these diseases are through the use of ELISA or immunodiffusion assays. The above flow cytometry method shortens turnaround times, decreases technical manipulations, increases sensitivity, eliminates the use of multiple plates, and decreases laboratory costs.

The above assay is a flow cytometric based procedure intended for the semi-quantitation of antibodies to RNP, Sm, SS-A(Ro), SS-B(La), and Scl-70. The results are reported in a semi-quantitative fashion using log fluorescense scales derived from the flow cytometers themselves. Gradations are strictly standardized against positive controls.

Principle and Procedure

Highly purified RNP, Sm, SS-A, SS-B, and Scl-70 antigen are bound to respective 4, 5, 6, 7 and 10 μm latex beads and stabilized for extended shelf life. Diluted patient's sera are placed into test tubes containing a mixture of the five antigen coated beads and incubated. If an antibody is present to the specific antigen (i.e. bead), it will bind to that specific bead. After washing the bead/sera mixture to remove residual sample, a second incubation with goat anti-human IgG conjugated with fluorescein isothiocyanate (FITC) is carried out. Conjugate will bind immunologically to the anti-antigen IgG of the antigen-antibody complex, forming a "sandwich" (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size (Y-axis) versus fluorescent intensity (X-axis, FIG. 2).

Kit Reagents and Components

|  | 50 TEST | 100 TEST |
| --- | --- | --- |
| Antigen Coated Beads (5 sizes) | 1 × 25 mL Coated with antigens to RNP, Sm, SS-A, SS-B, and Scl-70. | 2 × 25 mL |
| Negative Control | 1 × 1 mL Prepared from selected human sera that do not react with the above antigens. | 1 × 2 mL |
| Positive Control | 1 × 0.5 mL Prepared from selected human sera containing antibodies to above antigens. Ranges on label. | 1 × 1 mL |
| Sample diluent | 1 × 5 mL Color-coded blue | 2 × 5 mL |
| Conjugate* | 1 × 0.5 mL Color-coded pink | 1 × 1 mL |
| Wash Concentrate | 1 × 20 mL Prepare Wash Solution by adding 180 mL of distilled water to each 20 mL of concentrate. | 2 × 20 mL |
| Round Bottom Microtiter plate | 1 | 1 |

*Preserved with sodium azide.

These reagents should be stored at 2–8° C. Do not allow these reagents to contact the skin or eyes. If contact occurs, wash with copious amounts of water.

Other Materials

1. Multichannel pipettor
2. Timer
3. 500 mL graduated cylinder
4. 500 mL Wash Solution Reservoir
5. Distilled water
6. Test tubes
7. Single/multivolume pipettor
8. Centrifuge
9. Flow cytometer Precautions Handle samples, controls, and other materials that contact the sample, as potentially biohazardous. Each donor unit in the controls should have been found to be negative for hepatitis B surface antigen and HIV-1 antibodies by FDA-approved third generation tests. However, because no method can offer complete assurance that HIV-1, hepatitis B virus, or other infectious agents are absent, these materials should be handled at the Biosafety Level 2 as recommended for any potentially infectious serum or blood specimen in the Centers for Disease Control/National Institutes of Health manual "Biosafety in Microbiology and Biomedical Laboratories", 1984.

Never pipette by mouth.

Avoid contact with open skin.

Certain of the test kit reagents contain sodium azide as a preservative. Azides are reported to react with lead and copper in plumbing to form compounds that may detonate on percussion. When disposing of solutions containing sodium azide, flush drains with large volumes of water to minimize the build-up of metal-azide compounds.

Laboratory Quality Control

1. Do not mix or interchange reagents from different test kit lots.
2. Do not use reagents beyond their shelf life.
3. Incubation temperatures above or below the recommended 10–30° C. and incubation times other than those indicated may give erroneous results.
4. The present flow bead assay is a very sensitive technique. Pipetting, incubation and temperature errors will be magnified. Cross contamination between reagents or between microwells when diluting will invalidate the test. Reagents are color-coded for user convenience.
5. The washing procedure is very important and requires special attention. An improperly washed reaction tube may cause erroneous results.

Specimen Collection

Whole-blood (at least 0.5mL) should be collected in a non-anticoagulated, red top tube by accepted medical techniques. The serum is separated from the clot and refrigerated, 2–8° C., for short-term storage or stored frozen, −20° C., for long-term storage. Avoid multiple freeze-thaw cycles. Specimens containing visible particulate matter should be clarified by ultracentrion before testing. Grossly contaminated specimens should not be used.

Caution: Serum samples should not be heat-inactivated as this may cause false positive results.

Flow Cytometer Adjustments

|  | Ortho Cytoron | B/D FACScan | Coulter Profile |
|---|---|---|---|
| Frwd-Sc |  |  |  |
| Detector | 62 | E000 | N/A |
| AMP Gain | 1x | LOG | 10 |
| Rt-Sc |  |  |  |
| Detector | 30 | 3 LOG | 275 |
| AMP Gain | 1x | 300 LOG | 2 |
| LFL1 (FITC) |  |  |  |
| Detector | 70 | 535 | 865 |
| Detector | log | LOG | N/A |
| Sample Rate | low | Normal | 50 |

NOTE: Other models may vary slightly. These settings are meant as reference values only.

Detailed Procedure

Allow test components and patient samples to warm to room temperature before use. Return promptly to refrigerator after use.

1. Properly label sufficient numbers of test tubes to identify positive and negative controls and patient samples.
2. Add 500 µL of a solution containing each bead suspension into each of the labelled test tubes.
3. Prepare 1:20 dilutions of the Positive and Negative Controls, and the patient samples, by adding 10 µL of each to 190 µL of sample diluent (in test tubes or microtiter plate provided).
4. Mix sample dilutions gently by withdrawing and expelling in a pipette tip 2 or 3 times (microtiter plate) or vortexing.
5. Transfer 50 µL of each diluted control or patient sample into corresponding test tube.
6. Gently vortex and incubate at room temperature (20 to 30° C.) for 15 minutes.
7. Add 1 mL of Wash Solution to each test tube.
8. Centrifuge for 10 minutes at 1500 g at 2–8° C.
9. Carefully decant supernatant and gently resuspend bead pellet by hand.
10. Add one drop (50 µL) of fluorescenated conjugate to each tube.
11. Gently vortex and incubate for 15 minutes at room temperature in the dark.
12. Add 1 mL of Wash Solution to each tube.
13. Centrifuge for 10 minutes at 1500 g at 2–8° C.
14. Carefully decant supernatant and gently resuspend bead pellet by hand.
15. Add 1 mL of Wash Solution to each tube.
16. Analyze on flow cytometer.

NOTE: Analysis should be made within 2 hours of final staining.

Calculation of Results

The evaluation of specimens is based on a semi-quantitation of the fluorescent intensity. Gradations are directly related to the logarhythmic scale used on the FL1 x-axis. Samples will therefore be gated by two-parameter settings (e.g. forward angle light scatter and LFL 1). Position fluorescent cursor at 0.5 log units on the x-axis. This will determine the degree of positivity (FIG. 2). Round values to the nearest 0.5 of the log scale to determine bead results. RNP, Sm, SS-A, SS-B, and Scl-70 must be read by using the schematic below. Because of specific scatter properties, the sequence of Sm, and SS-A are reversed in some flow cytometers (e.g. CytoronAbsolute, Ortho). Therefore, the following table has been designed to assist the operator in assigning proper bead positions and results.

Bead Scatter Positions (From Lowest Scatter to Highest)

|  | Ortho Cytoron | B/D FACScan | Coulter Profile II |
|---|---|---|---|
| RNP (4 µm) | 1 | 1 | 1 |
| SM (5 µm) | 3 | 2 | 2 |
| SS-A (6 µm) | 2 | 3 | 3 |
| SS-B (7 µm) | 4 | 4 | 4 |
| Scl-70 (1.0µ) | 5 | 5 | 5 |

A negative control serum, when run with the assay kit, must fall within 0.5 log units of the LFL1 origin. Place a single vertical cursor from this point to indicate the region of positivity to the right (FIG. 3).

Figure 6:
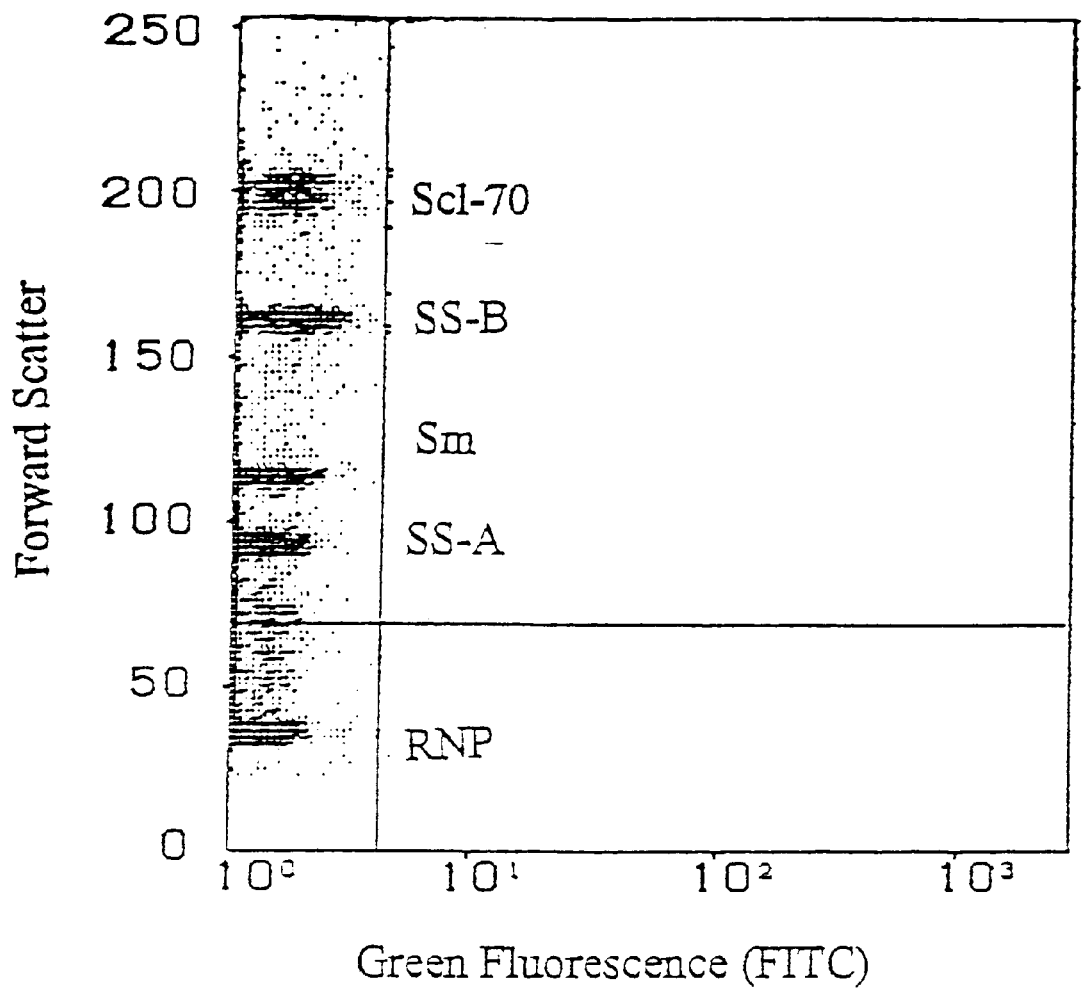
FIG. 6 is an illustration of a flow cytometer histogram of coated beads incubated with a negative control sample.

FIGS. 3 and 6—Negative Control

Figure 7:
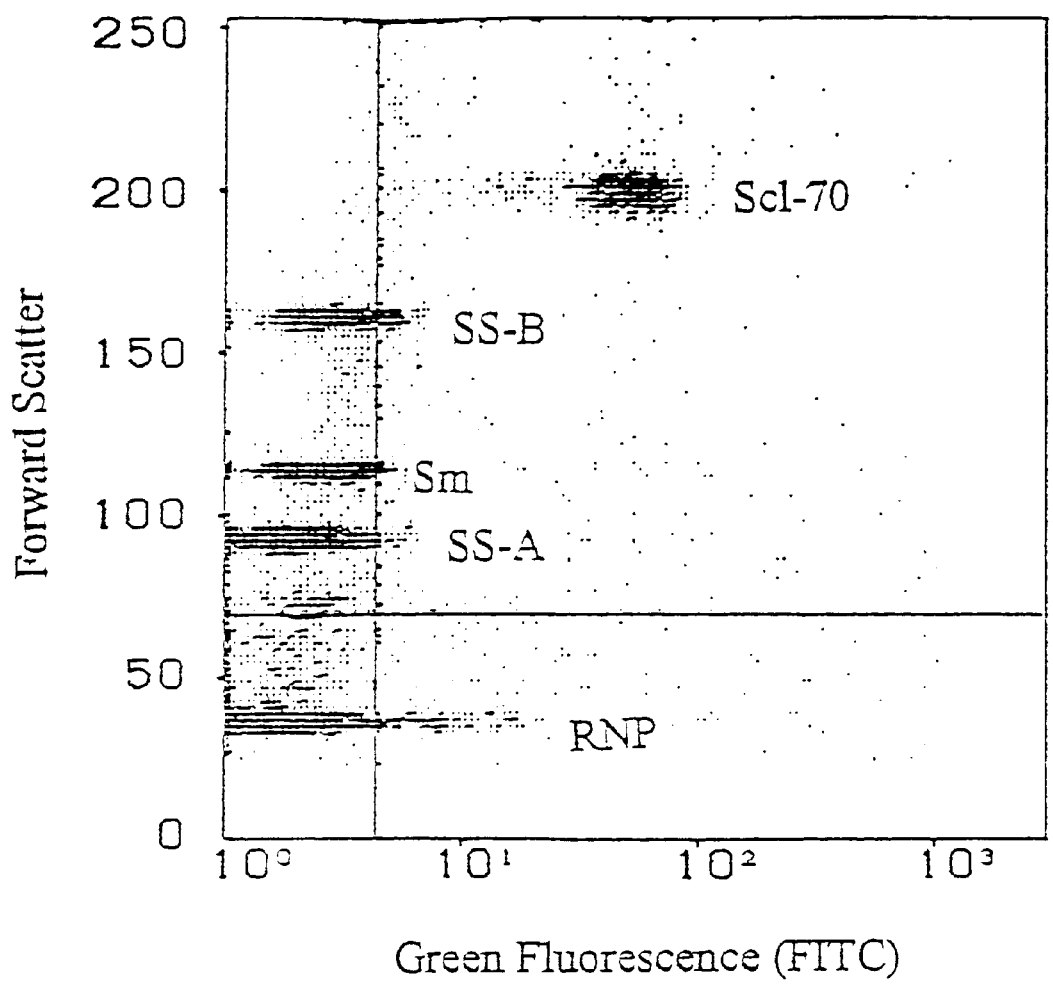
FIG. 7 is a representation of a flow cytometer histogram of a positive sample in which antibody to Scl-70 is present, but no antibodies to the other antigens are present.

All fluorescent intensity falling to the right of this region will be semi-quantitated according to the relative position on the LFL 1 log scale (e.g. 0.5, 1.0, 1.5, 2.0, 2.5, 3.0, 3.5, and 4.0 units FIG. 2 & 7).

FIG. 2—Positive Control Units

Patient samples which contain very high levels of antibody may give fluorescent results greater than 4.0 log units. If a more accurate semi-quantitative unit is necessary, dilute the patient sample using Sample Diluent, reassay, and report the result in log units while indicating the dilution factor.

Calibration

The assay reagents should be adjusted for optimal concentrations for the flow cytometers mentioned before. The positive control must fall within the ranges established for that lot. Slight variations in intensity may arise depending on a labs preference for gain and detector settings.

Figure 10:
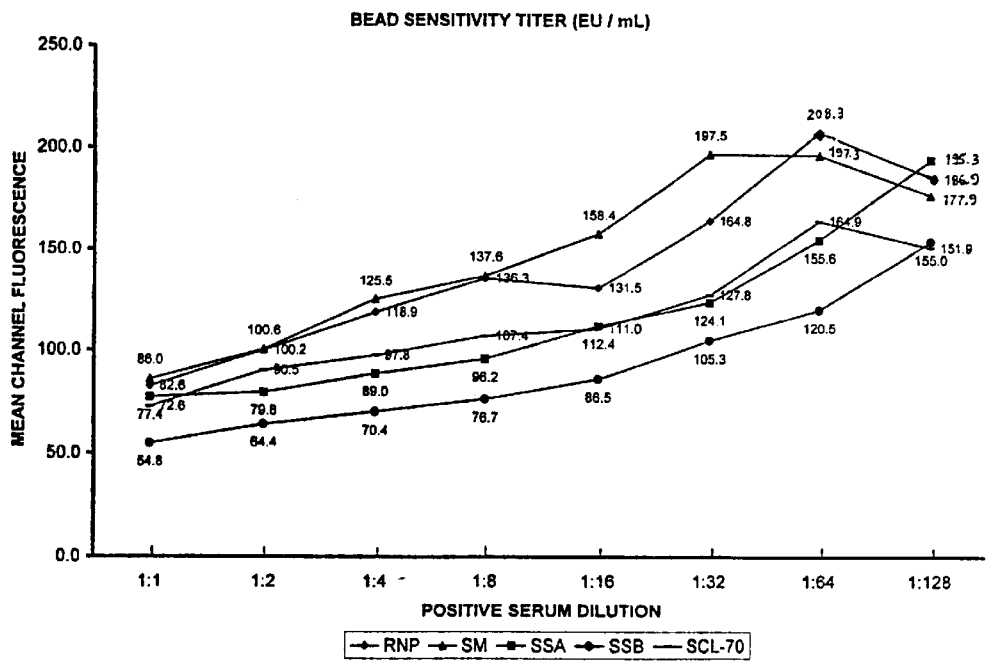
FIG. 10 is a tabular and graphical representation of flow cytometer assay sensitivity results of fluorescence versus positive serum dilution.
Figure 11:
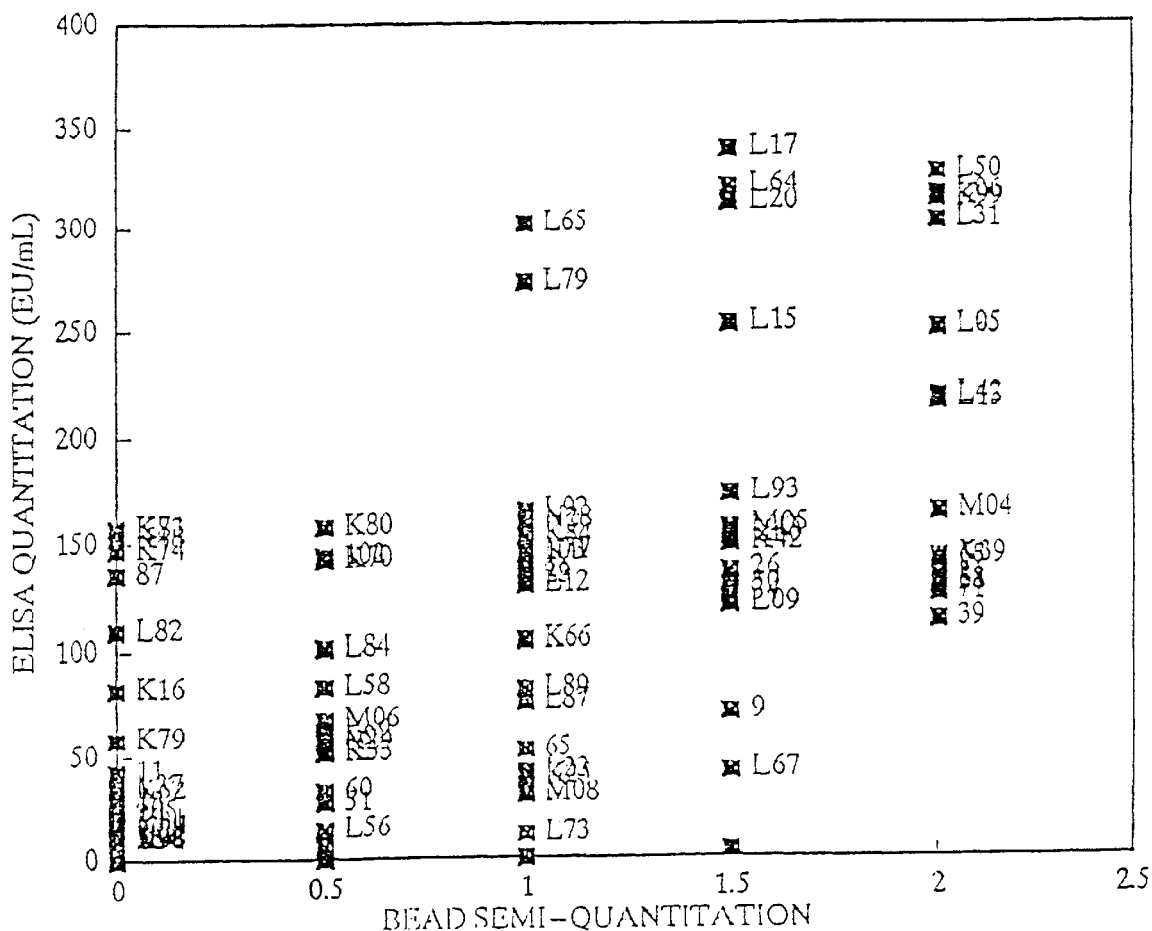
FIGS. 11–15 are graphical illustrations of comparative quantitation results of ELISA assay versus the double wash bead assay of the present invention relating to the respective antigens RNP, Sm, SS-A, SS-B, and Scl-70.
Figure 12:
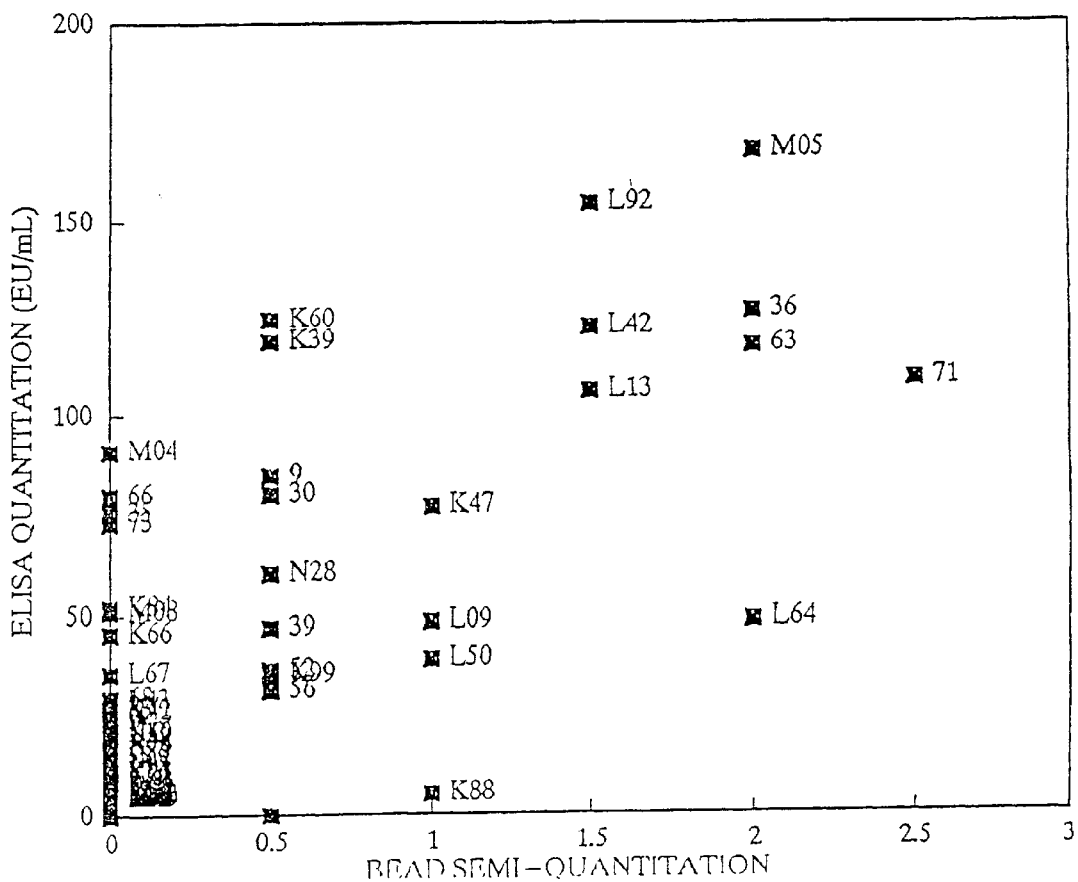
Figure 13:
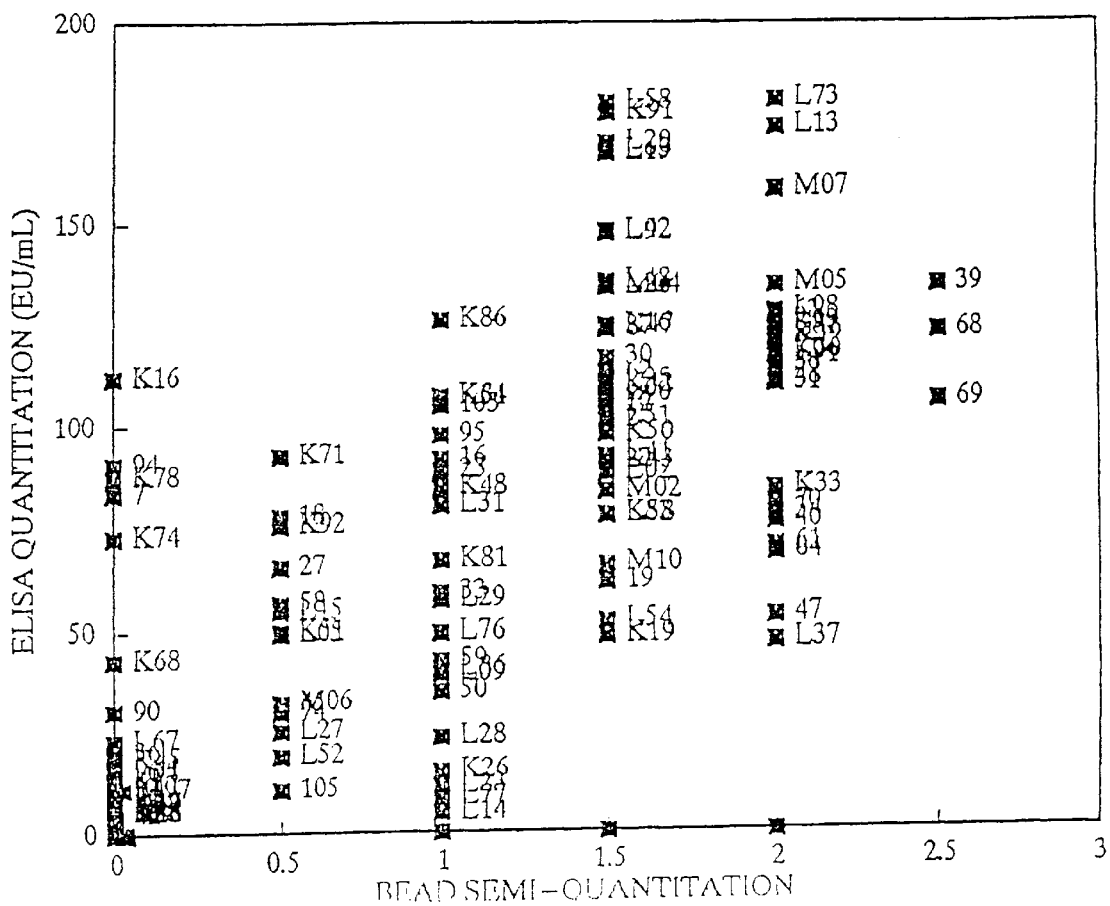
Figure 14:
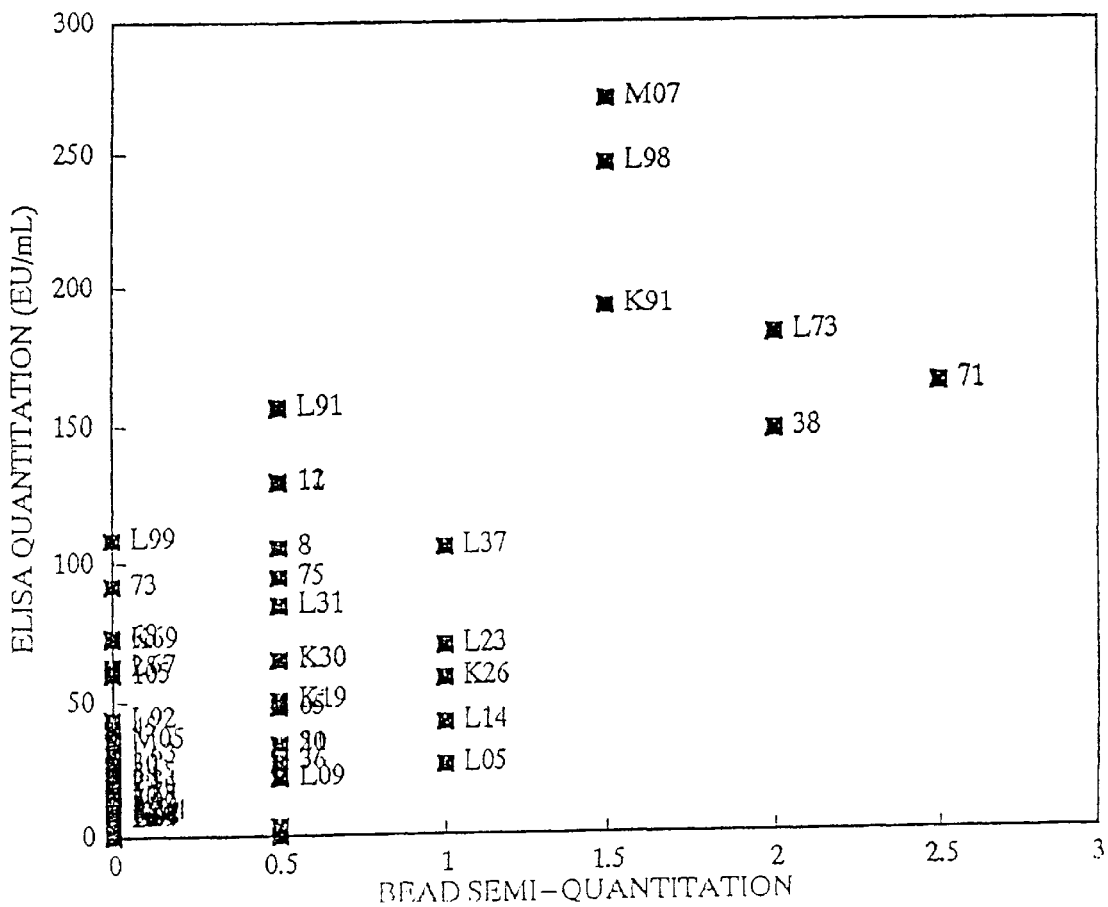
Figure 15:
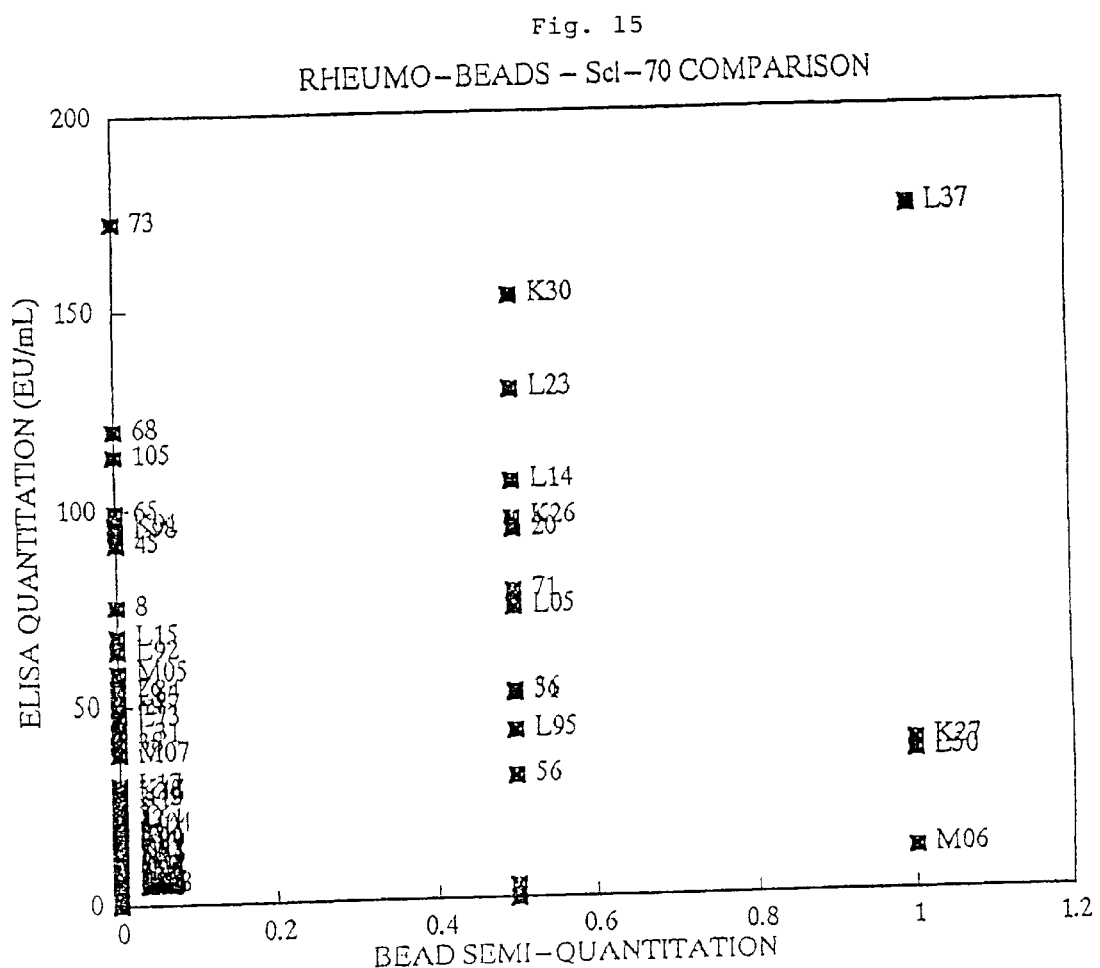
Figure 16:
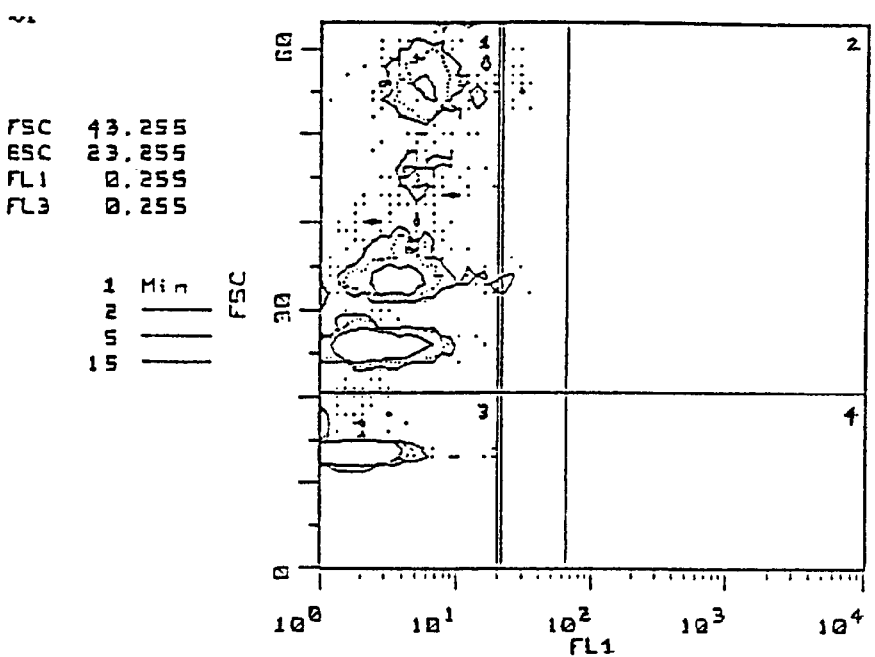
FIGS. 16–22 are graphical and tabular representations of flow cytometer results of seven runs of the double wash bead assay of the present invention using five different sizes of beads each coated with a particular Scl-70, SS-B, SS-A, Sm, and RNP antigen and positive beads labelled with goat anti-human IgG with FITC.
Figure 17:
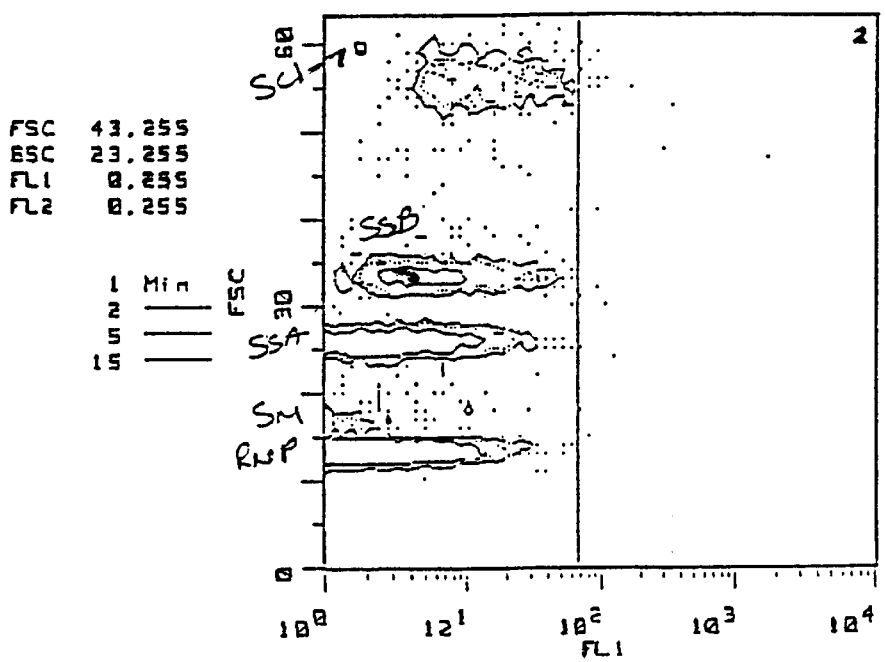
Figure 18:
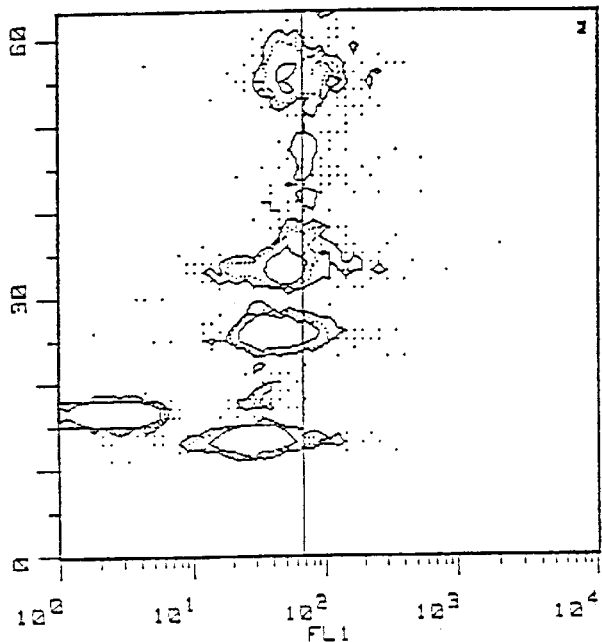
Figure 19:
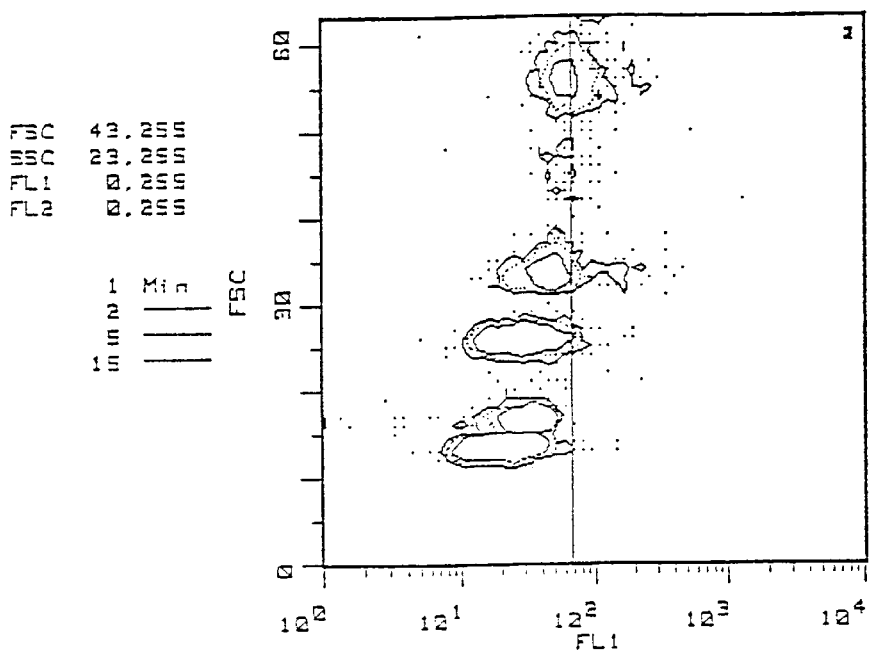
Figure 20:
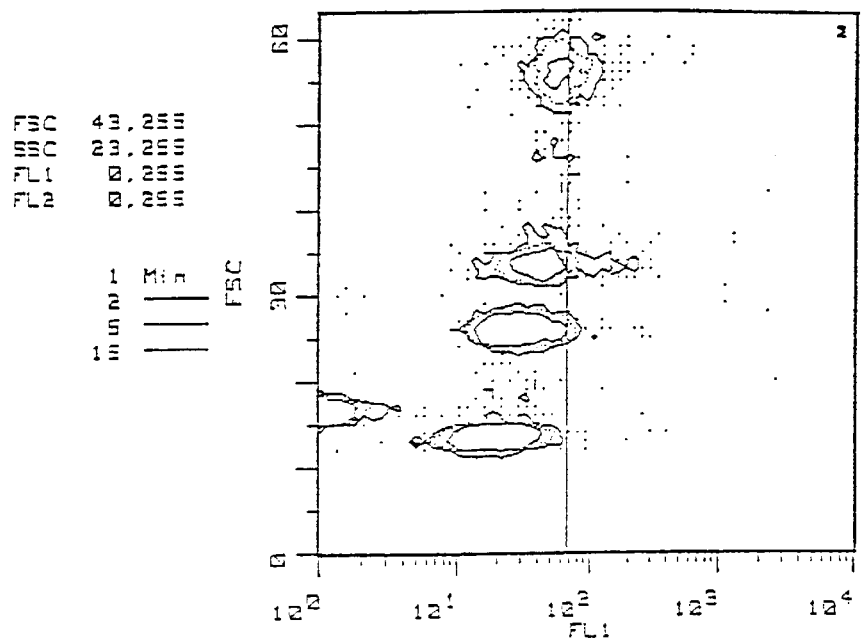
Figure 21:
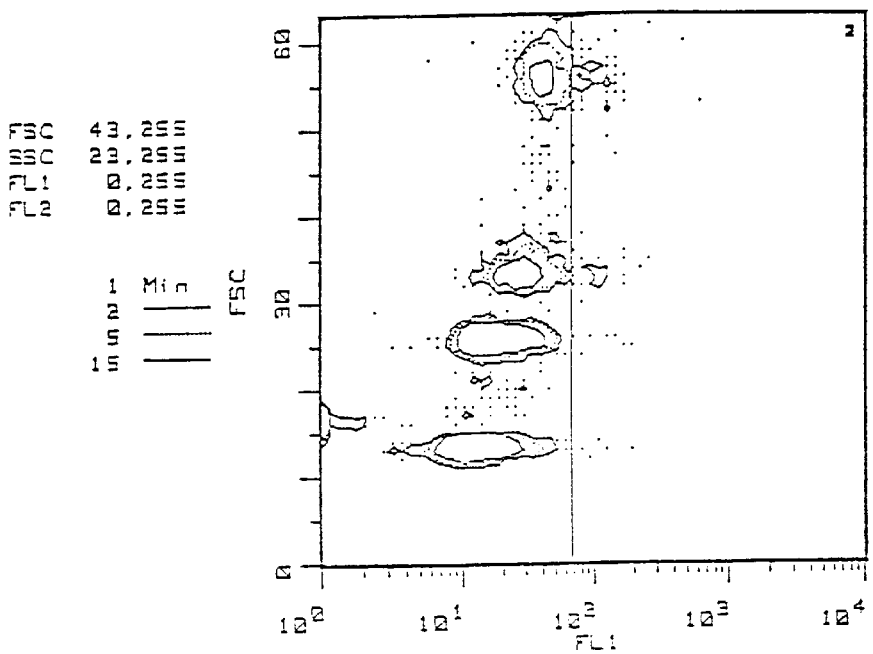
Figure 22:
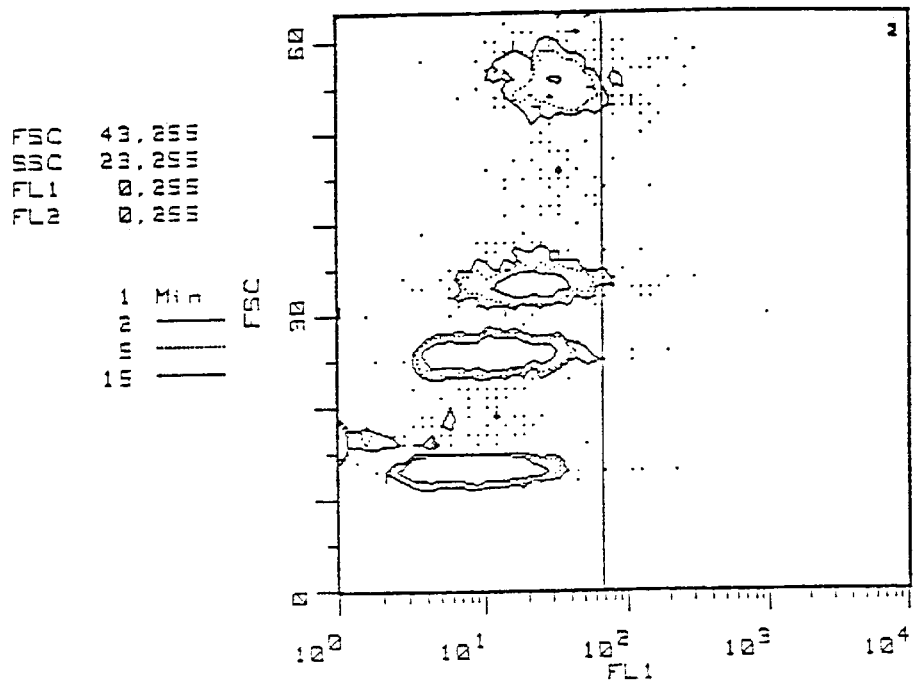

The beads should be evaluated for sensitivity against ELISA assays using known positives quantitated to international standards (EU/mL). All beads should be able to detect antibody concentrations of less then 0.5 EU/mL (See FIG. 10, Sensitivity Graph)

Test Validation Criteria a) The Positive and Negative Controls must be included in each test run as well as a bead blank.
b) The fluorescense intensity of the Positive Control must be 0.5 or greater.
c) The Positive Control and blank must fall below the 0.5 marker.
d) The Positive Control must give a semi-quantitative value within the range for that lot.

If any of these criteria are not met, the results are invalid and the test should be repeated.

Interpretation of Results

The following is a guide to interpretation. Each laboratory is encouraged to establish its own "normal" ranges based on populations encountered and flow cytometer sensitivity.

| General Bead Values | Interpretation |
|---|---|
| Less than 0.5 log units | Negative for antibodies |
| Greater than or equal to 0.5 units and less than 1.0 units | Equivocal for antibodies |
| Greater than or equal to 1.0 units | Positive for antibodies |

Before equivocal results are reported, retest the sample by the above described method or another approved method. Alternatively, obtain another sample from the same patient and retest. If repeated results are still equivocal, the test sample has no significant antibodies and should be reported as negative.

Limitations

The results of the present assay kit should be used in conjunction with clinical criteria for diagnosis of autoimmune rheumatic disease. While laboratory tests should not be used as dictators of therapy, they can be used to supplement clinical observations and as guides to therapy.

Expected Values

The negative range was determined from serum samples obtained from 50 normal blood donors which were assayed by the above assay. Forty-nine were negative for all antibodies while one was positive for RNP. The positive range (greater than 0.5 units) has been established by gain adjustments of various flow cytometric manufacturers instruments along with data obtained from 250 patients having SLE, Sjogren's Syndrome, Scleroderma, or MCTD with positive results obtained by secondary ELISA kits and confirmed by use of Diamedix Assays for the same antibodies. These results are seen in FIGS. 11–15. Patients, with some conditions, may express more than one anti-nuclear antibody, e.g., antibody to RNP may be seen in mixed connective tissue disease, SLE, Sjogren's syndrome, scleroderma, and polymyostitis, and SS-A and SS-B may be seen in Sjogren's syndrome and SLE.

EXAMPLE 12

Assay Kit
Kit Reagents and Components

| | 50 TEST | 100 TEST |
|---|---|---|
| Antigen Coated Beads (3 sizes, 10, 20, & 30 µm) | 1 × 25 mL Coated respectively with Histone antigens H2B, H3, H4 | 2 × 25 mL |
| Negative Control | 1 × 1 mL Prepared from selected human sera that do not react with the above antigens | 1 × 2 mL |
| Positive Control | 1 × 0.5 mL Prepared from selected human sera containing antibodies to above antigens. Ranges on label. | 1 × 1 mL |
| Sample diluent | 1 × 5 mL Color-coded blue. | 2 × 5 mL |
| Conjugate* | 1 × 0.5 mL Color-coded pink. | 1 × 1 mL |
| Wash Concentrate | 1 × 20 mL Prepare Wash Solution by adding 180 mL of distilled water to each 20 mL of concentrate. | 2 × 20 mL |
| Round Bottom Microtiter plate | 1 | 1 |

*Preserved with sodium azide.

EXAMPLE 13

Assay Kit
Kit Reagents and Components

| | 50 TEST | 100 TEST |
|---|---|---|
| Antigen Coated Beads (8 sizes, 2, 4, 6, 8, 10, 12, 14 & 16 µm) | 1 × 25 mL Coated respectively with RNP, Sm, SS-A, SS-B, Scl-70, Histone H1, Histone H2A and Proteinase 3 antigens | 2 × 25 mL |
| Negative Control | 1 × 1 mL Prepared from selected human sera that do not react with the above antigens | 1 × 2 mL |
| Positive Control | 1 × 0.5 mL Prepared from selected human sera containing antibodies to above antigens. Ranges on label. | 1 × 1 mL |
| Sample diluent | 1 × 5 mL Color-coded blue | 2 × 5 mL |
| Conjugate* | 1 × 0.5 mL Color-coded pink | 1 × 1 mL |
| Wash Concentrate | 1 × 20 mL Prepare Wash Solution by adding 180 mL of distilled water to each 20 mL of concentrate | 2 × 20 mL |
| Round Bottom Microtiter plate | 1 | 1 |

*Preserved with sodium azide.

These reagents should be stored at 2–8° C. Do not allow these reagents to contact the skin or eyes. If contact occurs, wash with copious amounts of water.

In accordance with the present invention it is preferred to use an Ortho CytoronAbsolute flow cytometer, but a Coulter Profile II, or Beaton/Dickinson, FCAScan can also be used. All instruments are operated using a 15 mw, air-cooled laser and the principles are identical.

Beads sizes may run from about 0.25 µm to 740.0 µm.

Other bead materials may include, polystyrene, glass, beads coated with different radical groups, metacrylate-styrene latex, traditional latex, polystyrene DVB. Possible fluorochromes include: Fluoresceine isothiocynate (FITC), Phycoerythrin (PE), Peridinin, Allochlorophyll (Per CP), Allophycocyanin, CY5, Texas Red, Propidium iodide, Ethidium bromide, and Acridine orange Antibodies which may be attached to beads or probes to detect antigens in body fluids include any monoclonal antibodies directed at infectious antigens such as, viruses, bacteria, parasites, fungi, and mycoplasma; autoantigens- (cell and cell components, such as nuclei, DNA, RNA nucleoli, membranes); cell products, such as collagen, reticulin, mucus, hormones, cytokines, neurotransmitters, coagulation factors, complement factors, mediators of inflammation (e.g. vasoconstructive, chematoctic, enzymatic, phospholy), and enzymes; cell membrane antigens (erythrocytes-cross match, HLA-transplantation), and spermatozoa.

DNA or RNA may be attached to beads as molecular probes for the detection of infectious agents, particularly viruses (EBV, CMV, HIV, varicella-zoster, hepatitis, HPV, HCV, HBV, HTLV), oncogens and other disease related genes, in fluids by molecular hybridization.

Many of the flow cytometers now have autobiosamplers which utilize robotic arms for multiple sampling. Likewise, the entire procedure may be placed on automated pipettors/dilutors prior to the actual analysis for large scale operations.

Semi-quantitative results can now be achieved by correlating the relative fluorescence to that of a 4 decade log histogram (0.5 or 1 log scale being the cut-off point of positivity). This is the same for any instrument used. Quantitative results may also be obtained by using pre-analyzed standards at specific EU/mL concentration.

Other examples of materials bound on beads:
a) Antigens—RnP, Sm, SS-A, SS-B, Scl-70
b) Antibodies—anti-p24, anti-htlv, OKT3
c) Chemicals—IL-2, Toxins, drugs
d) Microorganisms—$E.\ coli$, HTLV, viruses
e) Cell components—IL-2R, Glycoproteins
f) DNA—double stranded complement strands
g) RNA—viral RNA
h) Others—cardiolipin, pollen, metals, recombinant products EXAMPLE 14
Anti-Viral Screening Assay and Test Kit In accordance with still another embodiment of the present invention, an FIBA-FCM assay test kit is described as follows Summary of Procedure
1. Add 50 μL of sample to 500 μL of CMV, EBV, HBsAg, HBc, HTLV, HCV, HIV bead solution. Mix well.
2. Incubate at room temperature for 15 minutes.
3. Add 1 μL PBS to each tube.
4. Centrifuge tubes for 10 minutes at 1500 g.
5. Decant supernatant and gently resuspend bead pellet.
6. Place one drop of fluorescenated conjugate into each tube. Mix well.
7. Incubate at room temperature, in the dark, for 15 minutes.
8. Add 1 μL PBS to each tube.
9. Centrifuge for 10 minutes at 1500 g.
10. Decant supernatant and gently resuspend bead pellet.
11. Add 1 μL of PBS.
12. Read on flow cytometer.

Intended Use Of Kit

For the simultaneous detection of anti-antibodies to the antigens CMV, EBV, HBsAg, HBC, HIV, HTLV, HCV, in serum as an aid in the diagnosis of viral infection.

Summary and Explanation

Current approaches to the detection of auto-antibodies in these diseases are through the use of ELISA or immunodiffusion assays. The above flow cytometry method shortens turnaround times, decreases technical manipulations, increases sensitivity, eliminates the use of multiple plates, and decreases laboratory costs.

The above assay is a flow cytometric based procedure intended for the semi-quantitation of antibodies to HBsAg, HBC, EBV, HTLV, HCV, and HIV. The results are reported in a semi-quantitative fashion using log fluorescence scales derived from the flow cytometers themselves. Gradations are strictly standardized against positive controls.

Principle and Procedure

Highly purified CMV, EBV, HIV, HCV, HBsAg, HBC, and HTLV antigens are bound to respective 2, 3, 4, 5, 6, 7 and 10 μm latex beads and stabilized for extended shelf life. Diluted patient's sera are placed into test tubes containing a mixture of the seven antigen coated beads and incubated. If an antibody is present to the specific antigen (i.e. bead), it will bind to that specific bead. After washing the bead/sera mixture to remove residual sample, a second incubation with goat anti-human IgG conjugated with fluorescein isothiocyanate (FITC) is carried out. Conjugate will bind immunologically to the anti-antigen IgG of the antigen-antibody complex, forming a "sandwich" (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size (Y-axis) versus fluorescent intensity (X-axis)).

Kit Reagents and Components

|  | 50 TEST | 100 TEST |
| --- | --- | --- |
| Antigen Coated Beads (7 sizes) | 1 × 25 mL<br>Coated with recombenant antigens to CMV, EBV, HIV, HBsAg, HBC, HTLV, HCV | 2 × 25 mL |
| Negative Control | 1 × 1 mL<br>Prepared from selected human sera that do not react with the above antigens. | 1 × 2 mL |
| Positive Control | 1 × 0.5 mL<br>Prepared from selected human sera containing antibodies to above antigens. Ranges on label. | 1 × 1 mL |
| Sample diluent | 1 × 5 mL<br>Color-coded blue | 2 × 5 mL |
| Conjugate* | 1 × 0.5 mL<br>Color-coded pink | 1 × 1 mL |
| Wash Concentrate | 1 × 20 mL<br>Prepare Wash Solution by adding 180 mL of distilled water to each 20 mL of concentrate. | 2 × 20 mL |
| Round Bottom Microtiter plate | 1 | 1 |

*Preserved with sodium azide.

These reagents should be stored at 2–8° C. Do not allow these reagents to contact the skin or eyes. If contact occurs, wash with copious amounts of water.

Other Materials
1. Multichannel pipettor
2. Timer
3. 500 mL graduated cylinder
4. 500 mL Wash Solution Reservoir
5. Distilled water
6. Test tubes
7. Single/multivolume pipettor
8. Centrifuge
9. Flow cytometer Precautions Handle samples, controls, and other materials that contact the sample, as potentially biohazardous. Each donor unit in the controls should have been found to be negative for hepatitis B surface antigen and HIV-1 antibodies by FDA-approved third generation tests. However, because no method can offer complete assurance that HIV-1, hepatitis B virus, or other infectious agents are absent, these materials should be handled at the Biosafety Level 2 as recommended for any potentially infectious serum or blood specimen in the Centers for Disease Control/National Institutes of Health manual "Biosafety in Microbiology and Biomedical Laboratories", 1984.

Never pipette by mouth.

Avoid contact with open skin.

Certain of the test kit reagents contain sodium azide as a preservative. Azides are reported to react with lead and copper in plumbing to form compounds that may detonate on percussion. When disposing of solutions containing sodium azide, flush drains with large volumes of water to minimize the buildup of metal-azide compounds.

Laboratory Quality Control

1. Do not mix or interchange reagents from different test kit lots.
2. Do not use reagents beyond their shelf life.
3. Incubation temperatures above or below the recommended 10–30° C. and incubation times other than those indicated may give erroneous results.
4. The present flow bead assay is a very sensitive technique. Pipetting, incubation and temperature errors will be magnified. Cross contamination between reagents or between microwells when diluting will invalidate the test. Reagents are color-coded for user convenience.
5. The washing procedure is very important and requires special attention. An improperly washed reaction tube may cause erroneous results.

Specimen Collection

Whole-blood (at least 0.5 mL) should be collected in a non-anticoagulated, red top tube by accepted medical techniques. The serum is separated from the clot and refrigerated, 2–8° C., for short-term storage or stored frozen, –20° C., for long-term storage. Avoid multiple freeze-thaw cycles. Specimens containing visible particulate matter should be clarified by ultracentrion before testing. Grossly contaminated specimens should not be used.

Caution: Serum samples should not be heat-inactivated as this may cause false positive results.

Flow Cytometer Adjustments

|  | Ortho Cytoron | B/D FACScan | Coulter Profile |
|---|---|---|---|
| Frwd-Sc |  |  |  |
| Detector | 62 | E000 | N/A |
| AMP Gain | 1x | LOG | 10 |
| Rt-Sc |  |  |  |
| Detector | 30 | 3 LOG | 275 |
| AMP Gain | 1x | 300 LOG | 2 |
| LFL1 (FITC) |  |  |  |
| Detector | 70 | 535 | 865 |
| Detector | log | LOG | N/A |
| Sample Rate | low | Normal | 50 |

NOTE: Other models may vary slightly. These settings are meant as reference values only.

Detailed Procedure

Allow test components and patient samples to warm to room temperature before use. Return promptly to refrigerator after use.

1. Properly label sufficient numbers of test tubes to identify positive and negative controls and patient samples.
2. Add 500 μL of bead solution into each of the labelled test tubes.
3. Prepare 1:20 dilutions of the positive and negative controls, and the patient samples, by adding 10 μL of each to 190 μL of sample diluent (in test tubes or microtiter plate provided).
4. Mix sample dilutions gently by withdrawing and expelling in a pipette tip 2 or 3 times (microtiter plate) or vortexing.
5. Transfer 50 μL of each diluted control or patient sample into corresponding test tube.
6. Gently vortex and incubate at room temperature (20–30° C.) for 15 minutes.
7. Add 1 mL of wash solution to each test tube.
8. Centrifuge for 10 minutes at 1500 g at 2–8° C.
9. Carefully decant supernatant and gently resuspend bead pellet by hand.
10. Add one drop (50 μL) of fluorescenated conjugate to each tube.
11. Gently vortex and incubate for 15 minutes at room temperature in the dark.
12. Add 1 mL of wash solution to each tube.
13. Centrifuge for 10 minutes at 1500 g at 2–8° C.
14. Carefully decant supernatant and gently resuspend bead pellet by hand.
15. Add 1 mL of wash solution to each tube.
16. Analyze on flow cytometer.

NOTE: Analysis should be made within 2 hours of final staining.

EXAMPLE 15

Multiple Fluorescence Bead Assay

1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add antigen to each respective tube: (μg)

| Antigen (size bead, dye) | Drops/mL Buffer | Ag/mL Buffer |
|---|---|---|
| RNP (4 μm, FITC) | 3 | 30 |
| Sm (5 μm, FITC) | 3 | 10 |
| SS-A (6 μm, FITC) | 6 | 15 |
| SS-B (7 μm, PE) | 6 | 15 |
| Scl-70 (10 μm, PE) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Centrifuge, decant and gently resuspend beads.
10. Add 1 mL of carbonate buffer per original milliliters of antigen/bead solution.
11. Add 100 mL of each antigen/bead mixture to all reaction tubes.

12. Dilute positive, negative and patient serum 1:20 in PBS.
13. Add 50 μL of each serum diluted to appropriately labelled tube.
14. Vortex gently and incubate for 15 minutes at room temperature.
15. Wash once with 1 mL carbonate buffer.
16. Centrifuge, decant and gently resuspend beads.
17. Add 20 μL of goat anti-human IgG F(ab')$^2$-FITC 1:20 (NOTE: dilution may slightly vary from lot to lot, titer all new lots).
18. Gently vortex and incubate 15 minutes at room temperature.
19. Centrifuge, decant and gently resuspend beads.
20. Add 0.5 mL of carbonate buffer.
21. Read on flow cytometer.

EXAMPLE 16
Multiple Dye Bead Assay
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add a particular antigen to each respective tube (μg)

| Size bead, fluorescent dye | Drops/mL Buffer | Ag/mL Buffer |
|---|---|---|
| 4 μm, PE | 3 | 30 |
| 5 μm, PE | 3 | 10 |
| 6 μm, PE | 6 | 15 |
| 7 μm, FITC | 6 | 15 |
| 10 μm, FITC | 10 | 10 |
| 12 μm, FITC | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Dilute positive, negative and patient serum 1:20 in PBS.
13. Add 50 μL of each serum diluted to appropriately labelled tube.
14. Vortex gently and incubate for 15 minutes at room temperature.
15. Wash once with 1 mL carbonate buffer.
16. Repeat steps 5 and 6.
17. Add 20 μL of goat anti-human IgG F(ab')$^2$-FITC 1:20 (NOTE: dilution may slightly vary from lot to lot, titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 17
One Step Bead Detection System
No Wash Detection System

The following "no wash" procedure is a modification of the above bead evaluation method and utilizes an albumin step in the conjugate to eliminate non-specific staining resulting from increased patient serum protein concentrations.
1. Allow reagents to come to room temperature.
2. Gently invert antigen coated bead mixture until an even distribution of bead product is observed.
3. Label test tubes for Blanks Controls, and Patients.
4. Add 500 μL of multiple bead suspension to each tube.
5. Add 12.5 μL of serum to appropriate test tubes.
6. Add 50 μL of saline to blank tube.
7. Gently vortex and incubate for 15 minutes at room temperature.
8. Make a 1:20 dilution of anti-human monoclonal antibodies or polyclonal goat anti-human F(ab')$^2$ IgG FITC (or other fluorochrome) in 0.5% albumin in PBS.
9. Add 50 μL of diluted conjugate to each tube.
10. Gently vortex and incubate for 15 minutes at room temperature, in the dark.
11. Add 1 mL of PBS to each tube.
12. Analyze on flow cytometer.

EXAMPLE 18
No Wash Detection System
1. Allow reagents to come to room temperature.
2. Gently invert antigen coated bead mixture until an even distribution of bead product is observed.
3. Label test tubes for Blank, Controls, and Patients.
4. Add at least 100 μL of JO-1, PM-1, or dsDNA bead suspension to each tube.
5. Add at least 12.5 μL of serum to appropriate test tubes.
6. Add at least 10 μL of PBS to blank tube.
7. Gently vortex and incubate for at least 15 minutes at room temperature.
8. Make an at least 1:2 dilution of labelled anti-human antibodies in at least 0.2% albumin in PBS.
9. Add at least 10 μL of diluted conjugate to each tube.
10. Gently vortex and incubate for at least 15 minutes at room temperature, in the dark.
11. Add about 0.5 mL of PBS to each tube.
12. Analyze on flow cytometer.

EXAMPLE 19
Anti-SLE Screening Assay Test Kit

In accordance with still another embodiment of the present invention, an FIBA-FCM assay test kit is described as follows.
Summary of Procedure
1. Add 50 μL of sample to 500 μL of RNP, Sm, SS-A(Ro), SS-B(La), and Scl-70 coated bead solution. Mix well.
2. Incubate at room temperature for 15 minutes.
3. Add 1 μL PBS to each tube.

4. Centrifuge tubes for 10 minutes at 1500 g.
5. Decant supernatant and gently resuspend bead pellet.
6. Place one drop of fluorescenated conjugate into each tube. Mix well.
7. Incubate at room temperature, in the dark, for 15 minutes.
8. Add 1 μL PBS to each tube.
9. Centrifuge for 10 minutes at 1500 g.
10. Decant supernatant and gently resuspend bead pellet.
11. Add 1 μL of PBS.
12. Read on flow cytometer.

Intended Use Of Kit

For the simultaneous detection of anti-antibodies to the antigens RNP, Sm, SS-A(Ro), SS-B(La), and Scl-70 in serum as an aid in the diagnosis and of certain so-called rheumatic or connective tissue diseases, e.g. systemic lupus erythematosis (SLE), Sjogren's syndrome, scleroderma, and polymyositis. For in vitro Diagnostic Use.

Summary and Explanation

Current approaches to the detection of auto-antibodies in these diseases are through the use of ELISA or immunodiffusion assays. The above flow cytometry method shortens turnaround times, decreases technical manipulations, increases sensitivity, eliminates the use of multiple plates, and decreases laboratory costs.

The above assay is a flow cytometric based procedure intended for the semi-quantitation of antibodies to RNP, Sm, SS-A(Ro), SS-B(La), and Scl-70. The results are reported in a semi-quantitative fashion using log fluorescense scales derived from the flow cytometers themselves. Gradations are strictly standardized against positive controls.

Principle and Procedure

Highly purified RNP, Sm, SS-A, SS-B, and Scl-70 antigen are bound to respective 4, 5, 6, 7 and 10 μm latex beads and stabilized for extended shelf life. Diluted patient's sera are placed into test tubes containing a mixture of the five antigen coated beads and incubated. If an antibody is present to the specific antigen (i.e. bead), it will bind to that specific bead. After washing the bead/sera mixture to remove residual sample, a second incubation with goat anti-human IgG conjugated with fluorescein isothiocyanate (FITC) is carried out. Conjugate will bind immunologically to the anti-antigen IgG of the antigen-antibody complex, forming a "sandwich" (FIG. 1).

Unbound conjugate is removed in the subsequent washing step The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size (Y-axis) versus fluorescent intensity (X-axis, FIG. 2).

Kit Reagents and Components

|  | 50 TEST | 100 TEST |
| --- | --- | --- |
| Antigen Coated Beads (5 sizes) | 1 × 25 mL<br>Coated with antigens to RNP, Sm, SS-A, SS-B, and Scl-70. | 2 × 25 mL |
| Negative Control | 1 × 1 mL<br>Prepared from selected human sera that do not react with the above antigens. | 1 × 2 mL |
| Positive Control | 1 × 0.5 mL<br>Prepared from selected human sera containing antibodies to above antigens. Ranges on label. | 1 × 1 mL |
| Sample diluent | 1 × 5 mL<br>Color-coded blue | 2 × 5 mL |
| Conjugate* | 1 × 0.5 mL<br>Color-coded pink | 1 × 1 mL |
| Wash Concentrate | 1 × 20 mL<br>Prepare Wash Solution by adding 180 mL of distilled water to each 20 mL of concentrate. | 2 × 20 mL |
| Round Bottom Microtiter plate | 1 | 1 |

*Preserved with sodium azide.

These reagents should be stored at 2–8° C. Do not allow these reagents to contact the skin or eyes. If contact occurs, wash with copious amounts of water.

Other Materials
1. Multichannel pipettor
2. Timer
3. 500 mL graduated cylinder
4. 500 mL Wash Solution Reservoir
5. Distilled water
6. Test tubes
7. Single/multivolume pipettor
8. Centrifuge
9. Flow cytometer Precautions Handle samples, controls, and other materials that contact the sample, as potentially biohazardous. Each donor unit in the controls should have been found to be negative for hepatitis B surface antigen and HIV-1 antibodies by FDA-approved third generation tests. However, because no method can offer complete assurance that HIV-1, hepatitis B virus, or other infectious agents are absent, these materials should be handled at the Biosafety Level 2 as recommended for any potentially infectious serum or blood specimen in the Centers for Disease Control/National Institutes of Health manual "Biosafety in Microbiology and Biomedical Laboratories", 1984.

Never pipette by mouth.

Avoid contact with open skin.

Certain of the test kit reagents contain sodium azide as a preservative. Azides are reported to react with lead and copper in plumbing to form compounds that may detonate on percussion. When disposing of solutions containing sodium azide, flush drains with large volumes of water to minimize the build-up of metal-azide compounds.

Laboratory Quality Control
1. Do not mix or interchange reagents from different test kit lots.
2. Do not use reagents beyond their shelf life.
3. Incubation temperatures above or below the recommended 10–30° C. and incubation times other than those indicated may give erroneous results.
4. The present flow bead assay is a very sensitive technique. Pipetting, incubation and temperature errors will be magnified. Cross contamination between reagents or between microwells when diluting will invalidate the test. Reagents are color-coded for user convenience.
5. The washing procedure is very important and requires special attention. An improperly washed reaction tube may cause erroneous results.

Specimen Collection

Whole-blood (at least 0.5 mL) should be collected in a non-anticoagulated, red top tube by accepted medical techniques. The serum is separated from the clot and refrigerated, 2–8° C., for short-term storage or stored frozen, −20° C., for long-term storage. Avoid multiple freeze-thaw cycles. Specimens containing visible particulate matter should be clarified by ultracentrion before testing. Grossly contaminated specimens should not be used.

Caution: Serum samples should not be heat-inactivated as this may cause false positive results.

Flow Cytometer Adjustments

|  | Ortho Cytoron | B/D FACScan | Coulter Profile |
|---|---|---|---|
| Frwd-Sc |  |  |  |
| Detector | 62 | E000 | N/A |
| AMP Gain | 1x | linear | 10 |
| Rt-Sc |  |  |  |
| Detector | 30 | 3 LOG | 275 |
| AMP Gain | 1x | linear | 2 |
| LFL1 (FITC) |  |  |  |
| Detector | 70 | 535 | 865 |
| Detector | log | linear | N/A |
| Sample Rate | low | Normal | 50 |

NOTE: Other models may vary slightly. These settings are meant as reference values only. Using a linear scale increases the opportunity to add new bead sizes.

Detailed Procedure

Allow test components and patient samples to warm to room temperature before use. Return promptly to refrigerator after use.

1. Properly label sufficient numbers of test tubes to identify positive and negative controls and patient samples.
2. Add 500 $\mu$L of a solution containing each bead suspension into each of the labelled test tubes.
3. Prepare 1:20 dilutions of the Positive and Negative Controls, and the patient samples, by adding 10 $\mu$L of each to 190 $\mu$L of sample diluent (in test tubes or microtiter plate provided).
4. Mix sample dilutions gently by withdrawing and expelling in a pipette tip 2 or 3 times (microtiter plate) or vortexing.
5. Transfer 50 $\mu$L of each diluted control or patient sample into corresponding test tube.
6. Gently vortex and incubate at room temperature (20 to 30° C.) for 15 minutes.
7. Add 1 mL of Wash Solution to each test tube.
8. Centrifuge for 10 minutes at 1500 g at 2–8° C.
9. Carefully decant supernatant and gently resuspend bead pellet by hand.
10. Add one drop (50 $\mu$L) of fluorescenated conjugate to each tube.
11. Gently vortex and incubate for 15 minutes at room temperature in the dark.
12. Add 1 mL of Wash Solution to each tube.
13. Centrifuge for 10 minutes at 1500 g at 2–8° C.
14. Carefully decant supernatant and gently resuspend bead pellet by hand.
15. Add 1 mL of Wash Solution to each tube.
16. Analyze on flow cytometer.

NOTE: Analysis should be made within 2 hours of final staining.

Calculation of Results

The evaluation of specimens is based on a semi-quantitation of the fluorescent intensity. Gradations are directly related to the logarhythmic scale used on the FL1 x-axis. Samples will therefore be gated by two-parameter settings (e.g. forward angle light scatter and LFL 1). Position fluorescent cursor at 0.5 log units on the x-axis. This will determine the degree of positivity (FIG. 2). Round values to the nearest 0.5 of the log scale to determine bead results RNP, Sm, SS-A, SS-B, and Scl-70 must be read by using the schematic below. Because of specific scatter properties, the sequence of Sm, and SS-A are reversed in some flow cytometers (e.g. CytoronAbsolute, Ortho). Therefore, the following table has been designed to assist the operator in assigning proper bead positions and results.

Bead Scatter Positions (From Lowest Scatter To Highest)

|  | Ortho Cytoron | B/D FACScan | Coulter Profile II |
|---|---|---|---|
| RNP (4 $\mu$m) | 1 | 1 | 1 |
| SM (5 $\mu$m) | 3 | 2 | 2 |
| SS-A (6 $\mu$m) | 2 | 3 | 3 |
| SS-B (7 $\mu$m) | 4 | 4 | 4 |
| Scl-70 (1.0$\mu$) | 5 | 5 | 5 |

A negative control serum, when run with the assay kit, must fall within 0.5 log units of the LFL1 origin. Place a single vertical cursor from this point to indicate the region of positivity to the right (FIG. 3).

FIGS. 3 and 6—Negative Control

All fluorescent intensity falling to the right of this region will be semi-quantitated according to the relative position on the LFL 1 log scale (e.g. 0.5, 1.0, 1.5, 2.0, 2.5, 3.0, 3.5, and 4.0 units FIG. 2 & 7).

FIG. 2—Positive Control Unit

Patient samples which contain very high levels of antibody may give fluorescent results greater than 4.0 log units. If a more accurate semi-quantitative unit is necessary, dilute the patient sample using Sample Diluent, reassay, and report the result in log units while indicating the dilution factor.

Calibration

The assay reagents should be adjusted for optimal concentrations for the flow cytometers mentioned before. The positive control must fall within the ranges established for that lot. Slight variations in intensity may arise depending on a labs preference for gain and detector settings.

The beads should be evaluated for sensitivity against ELISA assays using known positives quantitated to international standards (EU/mL). All beads should be able to detect antibody concentrations of less then 0.5 EU/mL (See FIG. 10, Sensitivity Graph)

Test Validation Criteria a) The Positive and Negative Controls must be included in each test run as well as a bead blank.
b) The fluorescense intensity of the Positive Control must be 0.5 or greater.
c) The Positive Control and blank must fall below the 0.5 marker.
d) The Positive Control must give a semi-quantitative value within the range for that lot.

If any of these criteria are not met, the results are invalid and the test should be repeated.

Interpretation of Results

The following is a guide to interpretation. Each laboratory is encouraged to establish its own "normal" ranges based on populations encountered and flow cytometer sensitivity.

| General Bead Values | Interpretation |
|---|---|
| Less than 0.5 log units | Negative for antibodies |
| Greater than or equal to 0.5 units and less than 1.0 units | Equivocal for antibodies |
| Greater than or equal to 1.0 units | Positive for antibodies |

Before equivocal results are reported, retest the sample by the above described method or another approved method. Alternatively, obtain another sample from the same patient and retest. If repeated results are still equivocal, the test sample has no significant antibodies and should be reported as negative.

Limitations

The results of the present assay kit should be used in conjunction with clinical criteria for diagnosis of autoimmune rheumatic disease. While laboratory tests should not be used as dictators of therapy, they can be used to supplement clinical observations and as guides to therapy.

Expected Values

The negative range was determined from serum samples obtained from 50 normal blood donors which were assayed by the above assay. Forty-nine were negative for all antibodies while one was positive for RNP. The positive range (greater than 0.5 units) has been established by gain adjustments of various flow cytometric manufacturers instruments along with data obtained from 250 patients having SLE, Sjogren's Syndrome, Scleroderma, or MCTD with positive results obtained by secondary ELISA kits and confirmed by use of Diamedix Assays for the same antibodies. These results are seen in FIGS. 11–15. Patients, with some conditions, may express more than one anti-nuclear antibody, e.g., antibody to RNP may be seen in mixed connective tissue disease, SLE, Sjogren's syndrome, scleroderma, and polymyostitis, and SS-A and SS-B may be seen in Sjogren's syndrome and SLE.

EXAMPLE 20

Assay Kit
Kit Reagents and Components

| | 50 TEST | 100 TEST |
|---|---|---|
| Antigen Coated Beads (3 sizes, 10, 20, & 30 µm) | 1 × 25 mL Coated respectively with Histone antigens H2B, H3, H4 | 2 × 25 mL |
| Negative Control | 1 × 1 mL Prepared from selected human sera that do not react with the above antigens | 1 × 2 mL |
| Positive Control | 1 × 0.5 mL Prepared from selected human sera containing antibodies to above antigens. Ranges on label. | 1 × 1 mL |
| Sample diluent | 1 × 5 mL Color-coded blue. | 2 × 5 mL |
| Conjugate* | 1 × 0.5 mL Color-coded pink. | 1 × 1 mL |
| Wash Concentrate | 1 × 20 mL Prepare Wash Solution by adding 180 mL of distilled water to each 20 mL of concentrate. | 2 × 20 mL |
| Round Bottom Microtiter plate | 1 | 1 |

*Preserved with sodium azide.

EXAMPLE 21

Assay Kit
Kit Reagents and Components

| | 50 TEST | 100 TEST |
|---|---|---|
| Antigen Coated Beads (8 sizes, 2, 4, 6, 8, 10, 12, 14 & 16 µm) | 1 × 25 mL Coated respectively with RNP, Sm, SS-A, SS-B, Scl-70, Histone H1, Histone H2A and Proteinase 3 antigens | 2 × 25 mL |
| Negative Control | 1 × 1 mL Prepared from selected human sera that do not react with the above antigens | 1 × 2 mL |
| Positive Control | 1 × 0.5 mL Prepared from selected human sera containing antibodies to above antigens. Ranges on label. | 1 × 1 mL |
| Sample diluent | 1 × 5 mL Color-coded blue | 2 × 5 mL |
| Conjugate* | 1 × 0.5 mL Color-coded pink | 1 × 1 mL |
| Wash Concentrate | 1 × 20 mL Prepare Wash Solution by adding 180 mL of distilled water to each 20 mL of concentrate | 2 × 20 mL |
| Round Bottom Microtiter plate | 1 | 1 |

*Preserved with sodium azide.

These reagents should be stored at 2–8° C. Do not allow these reagents to contact the skin or eyes. If contact occurs, wash with copious amounts of water.

In accordance with the present invention it is preferred to use an Ortho CytoronAbsolute flow cytometer, but a Coulter Profile II, or Beaton/Dickinson, FCAScan can also be used. All instruments are operated using a 15 mw, air-cooled laser and the principles are identical.

Beads sizes may run from about 0.25 µm to 740.0 µm. Other bead materials may include, polystyrene, glass, beads coated with different radical groups, metacrylate-styrene latex, traditional latex, polystyrene DVB. The beads may themselves be impregnated with different fluorochromes. Possible fluorochromes include: Fluoresceine isothiocynate (FITC), Phycoerythrin (PE), Peridinin, Allochlorophyll (Per CP), Allophycocyanin, CY5, Texas Red, Propidium iodide, Ethidium bromide, and Acridine orange Antibodies which may be attached to beads or probes to detect antigens in body fluids include any monoclonal antibodies directed at infectious antigens such as, viruses, bacteria, parasites, fungi, and mycoplasma; autoantigens-(cell and cell components, such as nuclei, DNA, RNA nucleoli, membranes); cell products, such as collagen, reticulin, mucus, hormones, cytokines, neurotransmitters, coagulation factors, complement factors, mediators of inflammation (e.g. vasoconstructive, chematoctic, enzymatic, phospholy), and enzymes; cell membrane antigens (erythrocytes-cross match, HLA-transplantation), and spermatozoa.

DNA, RNA or other recombinant products may be attached to beads as molecular probes for the detection of infectious agents, particularly viruses (EBV, CMV, HIV, varicella-zoster, hepatitis, HPV, HCV, HBV, HTLV), oncogens and other disease related genes, in fluids by molecular hybridization.

Many of the flow cytometers now have autobiosamplers which utilize robotic arms for multiple sampling. Likewise, the entire procedure may be placed on automated pipettors/dilutors prior to the actual analysis for large scale operations.

Semi-quantitative results can now be achieved by correlating the relative fluorescence to that of a 4 decade log histogram (0.5 or 1 log scale being the cut-off point of positivity). This is the same for any instrument used. Quantitative results may also be obtained by using pre-analyzed standards at specific EU/mL concentration.

Other examples of materials bound on beads:
a) Antigens—RnP, Sm, SS-A, SS-B, Scl-70, Jo-1, dsDNA, PM-1
b) Antibodies—anti-p24, anti-htlv, OKT3
c) Chemicals—IL-2, Toxins, drugs
d) Microorganisms—*E.coli,* HTLV, viruses
e) Cell components—IL-2R, Glycoproteins
f) DNA—double stranded complement strands
g) RNA—viral RNA
h) Others—cardiolipin, pollen, metals, recombinant products

EXAMPLE 22

In accordance with another example of the present invention, one can conduct a chemistry panel or check for different concentrations of chemical substances using latex beads impregnated with different fluorescent dyes.

EXAMPLE 23

Further to Example 22 above, multiple panels can be used in conjunction with different size and color beads. For example, ten anti-ENA or SLE antigen detections, five sizes, two different fluorochromes, multiple bead colors.

EXAMPLE 24

Further, capture techniques including or like bacteria typing can be done using beads of different sizes and colors.

The present invention is directed to a kit, assay, and system for simultaneously detecting one or more antigens or analytes in a sample using a flow cytometer to analyze at least the size and the fluorescence of a plurality of separate, single microsphere complexes or "sandwiches" including, as described above and as shown for example in FIG. 1 of the drawings, a single bead carrier, a bound antigen or analyte, a primary antibody against the bound antigen, a secondary anti-species antibody attached to the primary antibody, and an indicator or fluorochrome attached to the anti-species antibody (one bead per complex or sandwich).

This single bead antigen-antibody complex or "sandwich" differs from an agglutination or aggregation assay wherein a plurality of beads are joined. In other words, the single bead "sandwich" or bead-antigen-antibody complex of the present invention only includes a single bead as contrasted to an aggregation or agglutination assay such as described in the Hansen reference The present invention is not directed to the use of an agglutination or aggregation assay wherein multiple beads or particles are combined to form groups or clumps to indicate positive assay results.

Flow Cytometry has the ability to distinguish between size and complexity of specifically sized particles (whether they be latex beads, cells, bacteria, or plankton). Complexity is defined as the amount of refracted light scattered and detected through sensitive photomultipliers (PMT's). In most cases, lasers supply the light and are placed perpendicular to the direction of the particle analysis stream. Size of particles is sensed through the "shadow" produced by the passing of a particle in front of the laser beam and detected by a PMT positioned directly opposite the light source.

It is respectfully believed that the present invention does not utilize "agglutination" techniques. Agglutination detection supposes that two or more particles will bind to form a "complex" which will be detected through increased 90 degree scatter properties. The present device does not rely on bead-bead interaction to detect positivity. In fact, it was difficult to create the present invention with the understanding that non-agglutination in flow cytometry applications is preferred, thus creating a uniqueness to the present invention.

The present invention utilizes the ability of the flow cytometer to distinguish single bead populations with fluorescence as the indicator, not agglutination.

With respect to the present application, please note:
1) the present kit uses surfactant coated latex beads and not polystyrene,
2) the present kit is stable for more than just "a few months", possibly a year or more,
3) McHugh et al. uses the sandwich-assay terminology as a capture technique using HRP coated beads, this is not an analytical device as outlined in the present application,
4) although McHugh et al. graphically represents FALS vs. FL1 and RALS vs. FL1, he only analyzes on FL1 each bead as indicated in the text (pg. 1, col. 3 bottom), and
5) McHugh et al. indicates that ability to detect analytes is dependent on size, whereas the present methodology does not and would benefit from fluorescent properties in conjunction with the bead size properties.

It is respectfully believed that the kit of the present invention has many positive and desirable features including components having a good shelf life stability, coated beads which do not clump, aggregate, or agglutinate, it utilizes dilutions similar to those of traditional IFA methodologies while still maintaining high specificity, it is especially adapted for clinical laboratory testing, it has versatility in that the kit may be used for testing on a number of flow cytometers with comparable results, it has modularity in that the beads can be packaged separately thus creating the potential for mix/match assays and the sizes of the beads may be selected at unique spacings to allow the addition of other assays, it is convenient to use, it does not require pre-dilutions, it can handle undiluted sera with negligible background, and the like.

Thus it will be appreciated that as a result of the present invention, a highly effective improved assay, kit and system, is provided by which the principal objective, among others, is completely fulfilled. It is contemplated, and will be apparent to those skilled in the art from the preceding description and accompanying drawings, that modifications and/or changes may be made in the illustrated embodiments without departing from the present invention. Accordingly, it is expressly intended that the foregoing description and accompanying drawings are illustrative of preferred embodiments only, not limiting, and that the true spirit and scope of the present invention be determined by reference to the appended claims.

TABLE I

Comparison of antibody detection by ELISA and Flow Cytometry (FC)

| Result | Antibody Detected | | | | |
|---|---|---|---|---|---|
| | nRNP | Sm | SSA | SSB | Scl-70 |
| Positive by ELISA and FC | 70 | 21 | 95 | 23 | 15 |
| Negative by ELISA and FC | 232 | 282 | 203 | 281 | 277 |
| Positive by ELISA Negative by FC | 11 | 15 | 6 | 12 | 25 |
| Negative by ELISA Positive by FC | 8 | 3 | 17 | 5 | 4 |
| Number of Samples | 321 | 321 | 321 | 321 | 321 |
| Overall Agreement | 94% | 94% | 93% | 95% | 91% |

This table summarizes the results of a comparison between an ELISA method and the Flow Cytometry method for detecting antibodies to nRNP, Sm, SSA, SSB, and Scl-70. It indicates the number of sample that gave the specified result for the antibody detected as well as the overall agreement of the two methods. Overall agreement is equal to (Positive by ELISA and FC+Negative by ELISA and FC)/Numeber of Samples.

REFERENCES

1. Alexander, E. L., et al. 1982, Ro(SSA) and La(SSB) antibodies in the clinical spectrum of Sjogren's Syndrome. *J. Rheumatol.* 9:239
2. Bonfa, E., et al. 1987, Association between Lupus Psychosis and Anti-Ribosomal p protein antibodies. *New Engl. J. Med.* 317:265.
3. Churg, *Systemic Vasculitis.*
4. Durata, N., Tan, E. M. (1976) Identification of antibodies to nuclear acidic antigens by counterimmunoelectrophoresis. *Arthritis Rheum.* 18:514.
5. Elkon, K. B., Jankowski, P. W. 1985. Fine specificities of autoantibodies directed against the Ro, La, Sm, RNP, and Jo-a proteins defined by two-dimensional gel electrophoresis and immunoblotting. *J. Rheumatol. No. 6.* 134:3819.
6. Elkon, K. B., Parnassa, A. P., Foster, C. L. 1985. Lupus auto-antibodies target ribosomal P proteins. *J. Exp. Med.* 162:459.
7. Franco, H. L., Weston, W. L., Peebles, C., et al. 1981. Auto-antibodies directed against the Sicca Syndrome antigens in the Neonatal Lupus Syndrome. *J. Am. Acad. Dermatol.* 4:67.
8. Fulwyler, M. J., McHugh, T. M., Flow Microsphere Immunoassay for the Quantitative and Simultaneous Detetction of Multiple Solube Analytes. In: Crissman H. A., Carzyneckiewica (eds): Methods in Cell Biology, New York; Academic Press 33:613–629, 1990.
9. Harley, J. B., Kaine, J. L., Fox, O. F., Reichlin, M., Gruber, B., Ro/SSA Antibody And Antigen in Congenital Complete Heart Block. University of Oklahoma Health Sciences Center. 1987.
10. Harley, J. B., Rosario, M. O., Yamagata, H., Fox, O. F., and Koren, E. Immunologic and Structural Studies of the Lupus/Sjogren's Syndrome Autoantigen, La/SSB, with a Monoclonal Antibody. J. Clin. Invest. Volume 76, August 1985.
11. Harley, J. B., Yamagata, H., Reichlin, M.: Anti-La/SSB Antibody is Present in Some Normal Sera and is Coincident with Ro/SSA Precipitins in Systemic Lupus Erythematosis. The Journal of Rheymatology, 11:3, 1984.
12. Herrera-Esparaza, R., Provost, T. T., Diaz, L. A. 1986. Molecular characterization of RO(SSA) and La(SSB) proteins. *J. Rheumatola.* 13:327.
13. Horan, P. K., Schenk, E. A., Abraham, G. N., Kloszewski, E. D., Fluid Phase Particle Fluorescence Analysis: Rheymatoid Factor Specificity Evaluated by Laser Flow Cytophotometry. In: Nakamur R. M., Dito, W. R., Tucker E. A. (eds): Immunoassays in the Clinical Laboratory, New York, Alan R. Liss pp 185–198, 1979.
14. Hudson, L., Hay, F. C. (1980), Practical Immunology. Black-well Scientific Publications, Oxford, England, p.237.
15. Kephart, D. C., Hood, A. F., Provost, T. T., 1981. Neonatal Lupus Erythematosis: New serologic findings. *J. Invest. Dermatol.* 77:331.
16. Lim, V. L., Gumbert, M., Carpvpu, R.; A Flow Cytometric Method for the Detection of the Development of Antibody to Orthoclone OKT3. J Immunol Methods 121:107–201, 1989.
17. Lindno, T., Bonner, O., Ugelstad, J., Nustad, K., Immunometric Assay by Flow Cytometry Using Mixtures of Two Particle Types of Different Affinity. J. Immunol Methods 126:183–189, 1990.
18. Maddison, P., Mogavero, H., Provost, T. T., Reichlin, M. 1979. The clinical significance of autoantibodies to a soluble cytoplasmic antigen in Systemic Lupus Erythematosis and other connective tissue diseases. *J. Rheumatol.* 9:239
19. McHugh, T. M., Milner, R. C., Logan, L. H., Stites, D. P., Simultaneous Detection of Antibodies to Cytomegalovirus and Herpes Simplex Virus by using Flow Cytometry and a Microsphere-Based Fluorescence Immunoassay. *J. Clin. Microbiol.* 26:1957–1961, 1988.
20. McHugh, T. M. and Stites, D. P., Application of Bead Based Assay for Flow Cytometry Analysis. Clinical Immunology Newsletter, 11, 60–64, 1991.
21. McHugh, T. M., Stites, D. P., Bush, M. P., et al. Relationship of Circulating Levels of Human Immunodeficiency Virus (HIV) Antigen, Antibody to p24, and HIV-Containing Immune Complexes in HIV-Infected Patients. J. Infect Dis. 158:1099–1091. 1988.
22. McHugh, T. M., Stites, D. P., Casavant, C. H., Fulwyler, M. J., Flow Cytometric Detection and Quantitation of Immune Complexes using Human Clq-coated Microspheres. *J. Immunol Methods,* 95:57–61, 1986.
23. McHugh, T. M., Wang, Y. J., Chong, H. O., Blackwood, L. L., Stites, D. P., Development of a Microsphere-Based Fluorescent Immunoassay and its Comparison to an Enzyme Immunoassay for the Detection of Antibodies to Three Antigen Preparations from Candida albicans. J. Immunol Methods 116:213–219, 1989.
24. Nakamura. *Autoantibodies to Nuclear Antigens.*
25. Netter, H. J., Guldner, H. H., Szostecki, C., Lakomek, H., Will H. 1987. A recombinant autoantigen derived from the human (U1) small nuclear RNP-specific 68-kD protein. *Arthritis Rheum.* 31:616.
26. Notman, D. D., Kurata, N., Tan, E. M., 1975. Profiles of antinuclear antibodies in Systemic Rheumatic Diseases. *Am. J. Med.* 83:464.
27. Rader, M. D., O'Brien, C., Liu, Y., Harley, J. B., Reichlin, M. 1989. Heterogeneity of the Ro/SSA antigen. *J. Clin. Invest.* 83:1293.
28. Sanders, G. C., Martin, J. C., Jett, J. H., Perkins, A.; Flow Cytometric Competitive Binding Assay for Determination of Actinomycin-D Concentrations. *Cytometry* 11:311–313, 1990.
29. Scilian, J. J., McHugh, T. M., Busch, M. P., et al., Early Detection of Antibodies Against rDNA-Produced HAV Proteins with a Flow Cytometric Assay. *Blood* 73:2041–2048, 1989.
30. Sharp, G. C., Irwin, W. S., Tan, E. M., et al. 1972. Mixed Connective Tissue Disease-An apparently distinct rheumatic disease syndrome associated with a specific antibody to an Extractable Nuclear Antigen (ENA). *Am. J. Med.* 52:148.
31. Shero, J. H., Bordwell, B., Rothfield, N. F., Earnshaw, W. C., 1985. High titers of autoantibodies to topoisomerase 1 (Scl-70) in sera from scleroderma patients. *Science.* 231:737.
32. Takano, M., Agris, P. F., Sharp, G. C., (1980) Purifications and biochemical characterization of nuclear ribonucleoprotein antigen using purified antibody from serum of a patient with mixed connective tissue disease. *J. Clinical Invest.* 66:1449.
33. Tan, et al. Autoantibodies to Nuclear Antigens. American Society of Clinical Pathologists Press, Chicago, 1985.
34. Tan, E. M. (Jan. 1983) Antinuclear antibodies in diagnosis and management, Hospital Practice: 79.
35. Tan, E. M., Dunkel, H. G. (1966), Characteristics of a soluble nuclear antigen precipitation with sera of patients with systemic lupus erythematosus. *J. of Inununol.* 96:464.
36. Tan, E. M., Fritzler, M. F., McDougal, J. S., McDuffie, F. C., Nakamura, R. M., Reichlin, M., Reimer, C. B., Sharp, G. C., Schur, P. H., Wilson, M. R., Winchester, R. J. (1982) Reference sera for antinuclear antibodies. *Arthritis Rheum.* 25:1003.
37. Tan, E. M., Peebles, C., (1976) Quantitation of antibodies to Sm antigen and nuclear ribonucleoprotein by hemagglutination, in Manual of Clinical Immunology (N.R. Rose and H. Friedman, eds.) Washington, D.C. Am Soc of Microbiol. p 660.
38. Tan, E. M., Rodman, G. P., Garcia, I., Moroi, Y., Fritzler, M. J., Peebles, C., (1980), Diversity of antinuclear antibodies in progressive systemic sclerosis. Anti-centromere antibody and its relationship to CREST syndrome. *Arthritis Rheum.* 23:617.
39. Van de Water, J., Cooper, A., Surh, C. D., Coppel, R., Danner, D., Ansari, A., Dickson, R., Gershwin, E. 1989. Detection of autoantibodies to recombinant mitochrondrial proteins in patients with Primary Biliary Cirrhosis. *N. Engl. J. Med. No.* 21. 320:1377.
40. Yang, G., Ulrich, P. P., Alyer, R. A., Rawal, B. C., Vyas, G. N., Detection of Hepatitis B Virus in Plasma Using Flow Cytometric Analysis of Polymerase Chain Reaction—Amplified DNA Incoprorating Digoxigenin-11-dUTP. *Blood* 81:1083–1088, 1993.

What is claimed is:

1. A fluorescent immuno-bead non-agglutination, sandwich assay kit for use in conjunction with flow cytometry for the simultaneous detection in sera of the antinuclear antibodies to RNP (ribonucleoprotein) selected from the group consisting of mixed connective disease, systemic lupus erythematosis (SLE), Sjogren's syndrome, scleroderma and polymyositis, Sm (Smith antigen) in SLE; SS-A in Sjogren's syndrome and SLE, SS-B in Sjogren's syndrome and SLE and Scl-70 in scleroderma, using a flow cytometer to analyze at least the size and the fluorescence of a plurality of single microsphere complexes each including a bead carrier, a bound antigen or analyte, a primary antibody against the bound antigen, a secondary anti-species antibody attached to the primary antibody, and an indicator attached to the anti-species antibody, comprising:

4 μm particle sized latex beads,
5 μm particle sized latex beads,
6 μm particle sized latex beads,
7 μm particle sized latex beads,
10 μm particle sized latex beads,
Sm/RNP Complex antigen,
Sm antigen,
SS-A (Ro) antigen,
SS-B (La) antigen,
Scl-70 antigen,
lyophilized Anti-RNP,
lyophilized Anti-Sm,
lyophilized Anti-SS-A (Ro)
lyophilized Anti-Sm,
lyophilized Anti-SSB (La)
lyophilized Anti-Scl-70.
Goat anti-human IgG F(ab')$^2$-[FITC] fluorescein isothiocyanlate,
Sodium Carbonate,
Sodium Bicarbonate, and
Bovine Serum Albumin.

2. A sandwich assay kit designed to simultaneously detect several anti-nuclear antibodies in patient sera utilizing antigen coated microspheres of different sizes, using a flow cytometer to analyze at least the size and the fluorescence of a plurality of single microsphere complexes each including a bead carrier, a bound antigen or analyte, a primary antibody against the bound antigen, a secondary anti-species antibody attached to the primary antibody, and an indicator attached to the anti-species antibody, comprising:

a) 4 μm latex beads coated with Sm/RNP complex antigen,
b) 5 μm latex beads coated with Sm antigen,
c) 6 μm latex beads coated with SS-A (Ro) antigen,
d) 7 μm latex beads coated with SS-B (La) antigen, and
e) 10 μm latex beads coated with Scl-70 antigen.

3. A non-agglutination, sandwich anti-SLE test kit for use with a flow cytometer to analyze at least the size and the fluorescence of a plurality of single microsphere complexes each including a bead carrier, a bound antigen or analyte, a primary antibody against the bound antigen, a secondary anti-species antibody attached to the primary antibody, and an indicator attached to the anti-species antibody, comprising:

five different sized antigen coated bead samples with a first sized bead being coated with an antigen to RNP, a second sized bead being coated with an antigen to Sm, a third sized bead being coated with an antigen to SS-A, a fourth size bead being coated with an antigen to SS-B, and a fifth sized bead being coated with an antigen to Scl-70, a negative control reagent prepared from selected human sera that do not react with the above antigens, a positive control reagent prepared from selected human sera containing antibodies to the above antigens, a sample diluent color-coded blue, a conjugate preserved with sodium azide and color-coded pink, and a wash concentrate adapted to be converted to a wash solution by adding a quantity of distilled water.

4. The anti-SLE kit as recited in claim 3 wherein said kit includes 25 ml bead samples, 1 ml of negative control reagent, 0.5 ml of positive control reagent, 5 ml of sample diluent, 0.5 ml of conjugate, 20 ml of wash concentrate, and one round bottom microtiter plate.

5. The anti-SLE kit as recited in claim 3 wherein said kit includes 50 ml bead samples 2 ml of negative control reagent, 1 ml of positive control reagent, 10 ml of sample diluent, 1 ml of conjugate, 40 ml of wash concentrate, and one round bottom microtiter plate.

6. An assay test kit for use in a non-agglutination, sandwich assay using a flow cytometer to analyze in sera at least the size and the fluorescence of a plurality of single microsphere complexes each including a bead carrier, a bound antigen or analyte, a primary antibody against the bound antigen, a secondary anti-species antibody attached to the primary antibody, and an indicator attached to the anti-species antibody, comprising:

a plurality of antigen coated bead samples each sample made up of a quantity of a respective different sized bead than the other samples and being coated with a respective different antigen than the other samples, a negative control reagent prepared from selected human sera that do not react with the above antigens, a positive control reagent prepared from selected human sera containing antibodies to the above antigens, a sample diluent, a conjugate preserved with sodium azide, and a wash concentrate adapted to be converted to a wash solution by adding a quantity of distilled water.

7. A non-agglutination, sandwich anti-SLE test kit for use with a flow cytometer to analyze at least the size and the fluorescence of a plurality of single microsphere complexes each including a bead carrier, a bound antigen or analyte, a primary antibody against the bound antigen, a secondary anti-species antibody attached to the primary antibody, and an indicator attached to the anti-species antibody, comprising:

eight different sized antigen coated bead samples with a first sized bead being coated with an antigen to RNP, a second sized bead being coated with an antigen to Sm, a third sized bead being coated with an antigen to SS-A, a fourth size bead being coated with an antigen to SS-B, and a fifth sized bead being coated with an antigen to Scl-70, a sixth sized bead coated with an antigen to Histone H1, a seventh sized bead coated with an antigen to Histone H2A, and an eighth sized bead coated with an antigen to Proteinase 3, a negative control reagent prepared from selected human sera that do not react with the above antigens, a positive control reagent prepared from selected human sera containing antibodies to the above antigens, a sample diluent color-coded blue, a conjugate preserved with sodium azide and color-coded pink, and a wash concentrate adapted to be converted to a wash solution by adding a quantity of distilled water.

8. The anti-SLE kit as recited in claim 7 wherein said kit includes 25 ml bead samples, 1 ml of negative control reagent, 0.5 ml of positive control reagent, 5 ml of sample diluent, 0.5 ml of conjugate, 20 ml of wash concentrate, and one round bottom microtiter plate.

9. The anti-SLE kit as recited in claim 7 wherein said kit includes 50 ml bead samples, 2 ml of negative control reagent, 1 ml of positive control reagent, 10 ml of sample diluent, 1 ml of conjugate, 40 ml of wash concentrate, and one round bottom microtiter plate.

10. Assay test kit for use in a non-agglutination, sandwich assay using a flow cytometer to analyze in sera at least the size and the fluorescence of a plurality of single microsphere complexes each including a bead carrier, a bound antigen or analyte, a primary antibody against the bound antigen, a secondary anti-species antibody attached to the primary antibody, and an indicator attached to the anti-species antibody, comprising:

a plurality of antigen coated bead samples each sample made up of a quantity of a respective different sized bead than the other samples and being coated with a respective different antigen than the other samples.

11. The test kit as recited in claim 10 further comprising:

a fluorecinated conjugate.

12. The test kit as recited in claim 10 further comprising:

a negative control reagent prepared from selected human sera that do not react with the above antigens, and a positive control reagent prepared from selected human sera containing antibodies to the above antigens.

* * * * *